(12) United States Patent
Taylor et al.

(10) Patent No.: US 11,547,428 B2
(45) Date of Patent: Jan. 10, 2023

(54) REDEPLOYABLE TISSUE RETRIEVAL SYSTEM

(71) Applicant: Applied Medical Resources Corporation, Rancho Santa Margarita, CA (US)

(72) Inventors: Scott V. Taylor, Rancho Santa Margarita, CA (US); Nicholas J. Fox, Rancho Santa Margarita, CA (US); Quoc P. Tran, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 78 days.

(21) Appl. No.: 17/098,202

(22) Filed: Nov. 13, 2020

(65) Prior Publication Data
US 2021/0145464 A1 May 20, 2021

Related U.S. Application Data

(60) Provisional application No. 62/936,128, filed on Nov. 15, 2019.

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00287* (2013.01);
(Continued)

(58) Field of Classification Search
CPC ............ A61B 17/00234; A61B 17/221; A61B 2017/00287; A61B 2017/00367; A61B 2017/2212
See application file for complete search history.

(56) References Cited

U.S. PATENT DOCUMENTS

| 30,471 A | 10/1860 | Dudley |
| 1,609,014 A | 11/1926 | Dowd |

(Continued)

FOREIGN PATENT DOCUMENTS

| CA | 2 628 969 C | 10/2009 |
| CN | 105662492 A | 6/2016 |

(Continued)

OTHER PUBLICATIONS

U.S. Pat. No. 5,853,374, filed Oct. 11, 1995 entitled Tissue Retrieval System and associated file history (now abandoned).
(Continued)

*Primary Examiner* — Mohamed G Gabr
(74) *Attorney, Agent, or Firm* — John F. Heal

(57) ABSTRACT

A tissue retrieval system including a tissue retrieval bag deployable by an actuator from an introducer and suspended in an open configuration by support arms can be serially redeployed between a partially or fully stowed configuration and a first deployed configuration to be used in procedures to collect multiple samples. The system can include defeasible proximal and distal stop mechanisms to limit movement of the actuator for serial redeployment. The tissue retrieval system can include a retention latch to couple a bead of the tissue retrieval bag to the actuator with the retrieval bag in the first deployed position and a user-selectable deployment release to allow deployment of the retrieval bag to a fully deployed position where it is released from the actuator. A bead stop is positioned to engage the introducer to prevent reintroduction of the bead and bag into the introducer once the bag has been fully deployed.

14 Claims, 33 Drawing Sheets

(52) U.S. Cl.
CPC ............... *A61B 2017/00367* (2013.01); *A61B 2017/2212* (2013.01)

(56) References Cited

U.S. PATENT DOCUMENTS

| | | | |
|---|---|---|---|
| 3,476,114 A | 11/1969 | Shannon et al. |
| 3,476,115 A | 11/1969 | Graeff et al. |
| 4,287,807 A | 9/1981 | Pacharis |
| 4,428,375 A | 1/1984 | Ellman |
| 4,732,150 A | 3/1988 | Keener Jr. |
| 4,741,335 A | 5/1988 | Okada |
| 4,807,626 A | 2/1989 | McGirr |
| 4,991,593 A | 2/1991 | Levahn |
| 5,037,379 A | 8/1991 | Clayman et al. |
| 5,074,867 A | 12/1991 | Wilk |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,195,507 A | 3/1993 | Bilweis |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,279,548 A | 1/1994 | Essig et al. |
| 5,308,327 A | 5/1994 | Heaven et al. |
| 5,312,416 A | 5/1994 | Spaeth et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,366,460 A | 11/1994 | Eberbach |
| 5,368,597 A | 11/1994 | Pagedas |
| 5,417,684 A | 5/1995 | Jackson et al. |
| 5,417,697 A | 5/1995 | Wilk et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| RE35,164 E | 3/1996 | Kindberg et al. |
| 5,509,923 A | 4/1996 | Middleman et al. |
| 5,524,633 A | 6/1996 | Heaven et al. |
| 5,535,759 A | 7/1996 | Wilk |
| 5,601,572 A | 2/1997 | Middleman et al. |
| 5,611,803 A | 3/1997 | Heaven et al. |
| 5,613,973 A | 3/1997 | Jackson et al. |
| 5,632,746 A | 5/1997 | Middleman et al. |
| 5,643,283 A | 7/1997 | Younker |
| 5,647,372 A | 7/1997 | Tovey et al. |
| 5,655,657 A | 8/1997 | Roshdy |
| 5,656,012 A | 8/1997 | Sienkiewicz |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,749,879 A | 5/1998 | Middleman et al. |
| 5,759,187 A | 6/1998 | Nakao et al. |
| 5,779,716 A | 7/1998 | Cano et al. |
| 5,782,839 A | 7/1998 | Hart et al. |
| 5,785,677 A | 7/1998 | Auweiler |
| 5,788,709 A | 8/1998 | Riek et al. |
| 5,809,621 A | 9/1998 | McCree et al. |
| 5,820,628 A | 10/1998 | Middleman et al. |
| 5,836,953 A | 11/1998 | Yoon |
| 5,853,374 A | 12/1998 | Hart et al. |
| 5,904,690 A | 5/1999 | Middleman et al. |
| 5,947,978 A | 9/1999 | Holsinger |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,015,415 A | 1/2000 | Avellanet |
| 6,019,770 A | 2/2000 | Christoudias |
| 6,059,793 A | 5/2000 | Pagedas |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,350,267 B1 | 2/2002 | Stefanchik |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,575,988 B2 | 6/2003 | Rousseau |
| 6,805,699 B2 | 10/2004 | Shimm |
| 6,814,739 B2 | 11/2004 | Secrest et al. |
| 6,958,069 B2 | 10/2005 | Shipp et al. |
| 6,986,774 B2 | 1/2006 | Middleman et al. |
| 7,041,055 B2 | 5/2006 | Young et al. |
| 7,101,379 B2 | 9/2006 | Gregory, Jr. et al. |
| 7,115,125 B2 | 10/2006 | Nakao et al. |
| 7,270,663 B2 | 9/2007 | Nakao |
| 7,547,310 B2 | 6/2009 | Whitfield |
| 7,615,013 B2 | 11/2009 | Clifford et al. |
| 7,618,437 B2 | 11/2009 | Nakao |
| 7,670,346 B2 | 3/2010 | Whitfield |
| 7,722,626 B2 | 5/2010 | Middleman et al. |
| 8,062,306 B2 | 11/2011 | Nobis et al. |
| 8,097,001 B2 | 1/2012 | Nakao |
| 8,282,572 B2 | 10/2012 | Bilsbury |
| 8,337,510 B2 | 12/2012 | Rieber et al. |
| 8,652,147 B2 | 2/2014 | Hart |
| 9,005,215 B2 | 4/2015 | Grover et al. |
| 9,826,997 B2 | 11/2017 | Cherry et al. |
| 10,154,833 B2 | 12/2018 | Holsten et al. |
| 10,335,130 B2 | 7/2019 | Ceniccola et al. |
| 10,772,614 B2 | 9/2020 | Holsten et al. |
| 2003/0100919 A1 | 5/2003 | Hopkins et al. |
| 2004/0087969 A1 | 5/2004 | Kayan |
| 2004/0097960 A1 | 5/2004 | Terachi et al. |
| 2004/0138587 A1 | 7/2004 | Lyons, IV |
| 2004/0254573 A1 | 12/2004 | Dycus et al. |
| 2005/0165411 A1 | 7/2005 | Orban, III |
| 2005/0267489 A1 | 12/2005 | Secrest et al. |
| 2005/0267492 A1 | 12/2005 | Poncet et al. |
| 2006/0052799 A1 | 3/2006 | Middleman et al. |
| 2006/0173468 A1 | 8/2006 | Simmon et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0276805 A1 | 12/2006 | Yu |
| 2007/0088370 A1 | 4/2007 | Kahle et al. |
| 2008/0033451 A1 | 2/2008 | Rieber et al. |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2009/0043315 A1 | 2/2009 | Moon |
| 2009/0082779 A1 | 3/2009 | Nakao |
| 2009/0019251 A1 | 7/2009 | Bahney |
| 2009/0306683 A1 | 12/2009 | Zwolinski et al. |
| 2010/0076451 A1 | 3/2010 | Zwolinski et al. |
| 2010/0152609 A1 | 6/2010 | Zwolinski et al. |
| 2010/0152746 A1 | 6/2010 | Ceniccola et al. |
| 2013/0190773 A1* | 7/2013 | Carlson ............ A61B 17/00234 606/114 |
| 2018/0221039 A1 | 8/2018 | Shah |
| 2019/0008496 A1 | 1/2019 | Taylor et al. |
| 2019/0083116 A1 | 3/2019 | Mansfield et al. |
| 2019/0336152 A1 | 11/2019 | Ahluwalia et al. |
| 2020/0113556 A1 | 4/2020 | Paulus et al. |

FOREIGN PATENT DOCUMENTS

| | | |
|---|---|---|
| CN | 106137278 A | 11/2016 |
| CN | 110537943 A | 12/2019 |
| DE | 25796 | 1/1884 |

(56) References Cited

FOREIGN PATENT DOCUMENTS

| | | |
|---|---|---|
| DE | 42 16 165 A1 | 11/1992 |
| DE | 197 07 361 A1 | 8/1998 |
| EP | 0 499 243 A1 | 8/1992 |
| EP | 0 947 166 A2 | 10/1999 |
| EP | 1 679 040 A1 | 7/2006 |
| EP | 1 707 126 A1 | 10/2006 |
| EP | 2 617 365 A2 | 7/2013 |
| JP | 05115493 A | 5/1993 |
| JP | 06154161 A | 6/1994 |
| SU | 1537229 A | 1/1990 |
| WO | WO 1993/15671 A1 | 8/1993 |
| WO | WO 1993/24063 A1 | 12/1993 |
| WO | WO 1994/13215 A2 | 6/1994 |
| WO | WO 99/53851 A1 | 10/1999 |
| WO | WO 03/105674 A2 | 12/2003 |
| WO | WO 2007/081601 A2 | 7/2007 |
| WO | WO 2008/114234 A2 | 9/2008 |
| WO | WO 2016/1199311 A1 | 8/2016 |
| WO | WO 2020/102714 A2 | 5/2020 |

OTHER PUBLICATIONS

U.S. Appl. No. 11/549,701, filed Oct. 16, 2006, entitled "Laparoscopic Tissue Retrieval System" and associated file history.

U.S. Appl. No. 11/549,971, filed Oct. 16, 2006 entitled Tissue Retrieval System and associated file history.

U.S. Appl. No. 12/902,055, filed Oct. 11, 2010 entitled "Single Incision Laparoscopic Tissue Retrieval System" and associated file history.

U.S. Appl. No. 13/252,110, filed Oct. 3, 2011, entitled "Laparoscopic Tissue Retrieval System" and associated file history.

European Patent Office, International Search Report and Written Opinion of the International Searching Authority for International Application No. PCT/US2006/060007, dated Mar. 2, 2007, 13 pgs.

The International Bureau of WIPO, The International Preliminary Report on Patentability for International Application No. PCT/US2006/060007 dated Apr. 24, 2008, 8 pgs.

European Patent Office, International Search Report and Written Opinion of the International Searching Authority for International Application No. PCT/US2006/060022, dated Jun. 5, 2007, 17 pgs.

The International Bureau of WIPO, The International Preliminary Report on Patentability for International Application No. PCT/US2006/060022, dated Jul. 24, 2008, 10 pgs.

International Searching Authority, International Search Report and Written Opinion for International Application No. PCT/US2010/052190, entitled "Single Incision Laparoscopic Tissue Retrieval System", dated Feb. 3, 2011, 11 pgs.

The International Bureau of WIPO, The International Preliminary Report on Patentability for International Application No. PCT/US2010/052190, entitled "Single Incision Laparoscopic Tissue Retrieval System," dated Apr. 11, 2012, 5 pgs.

International Searching Authority, International Search Report and Written Opinion for International Application No. PCT/US2011/054647, entitled "Laparoscopic Tissue Retrieval System," dated Feb. 21, 2012, 8 pgs.

International Searching Authority, International Preliminary Reporton Patentability for International Application No. PCT/US2011/054647, entitled "Laparoscopic Tissue Retrieval System," dated Apr. 16, 2013, 6 pgs.

European Patent Office, Extended European Search Report for European Patent Application No. EP 19177060.1, titled "Single Incision Laparoscopic Tissue Retrieval System," dated Sep. 16, 2019, 10 pgs.

United States Surgical, Tyco Healthcare Group LP, Autosuture *Endo Catch* Single-Use Specimen Pouch, Frequently Asked Questions and Features and Benefits (web pages), 2004, 4 pgs.

United States Surgical, Tyco Healthcare Group LP, Autosuture* Endocatch* Gold 10 mm Single-Use Specimen Pouch, 10000-25912, Product Information Data Sheet, Feb. 2004, 2 pgs.

United States Surgical, Tyco Healthcare Group LP, Autosuture* Endocatch* II Single-Use Specimen Pouch, 10000-19724, Product Information Datasheet, Aug. 2002, 2 pgs.

Conmed Corporation, EndoSurgery Products, Hand Held Laparoscopic Instruments, Product Descriptions (Web pages), 2004, 3 pgs.

Cook Group Inc., Cook Urological, Cook® Drainage Pouch Sets, Product Description (Web page), 2003, 1 page.

Johnson & Johnson Gateway LLC, Ethicon Endo-Surgery Inc., Endoscopic Product Family, Endopouch Retriever Specimen Retrieval Bag, Product Description (Web Page), 2000-2005, 1 pg.

International Searching Authority, International Search Report and Written Opinion for International Application No. PCT/US2020/060592, entitled "Redeployable Tissue Retrieval System," dated Apr. 13, 2021, 17 pgs.

International Searching Authority, International Preliminary Report on Patentability for International Application No. PCT/US2020/060592, entitled "Redeployable Tissue Retrieval System," dated May 27, 2022, 11 pgs.

\* cited by examiner

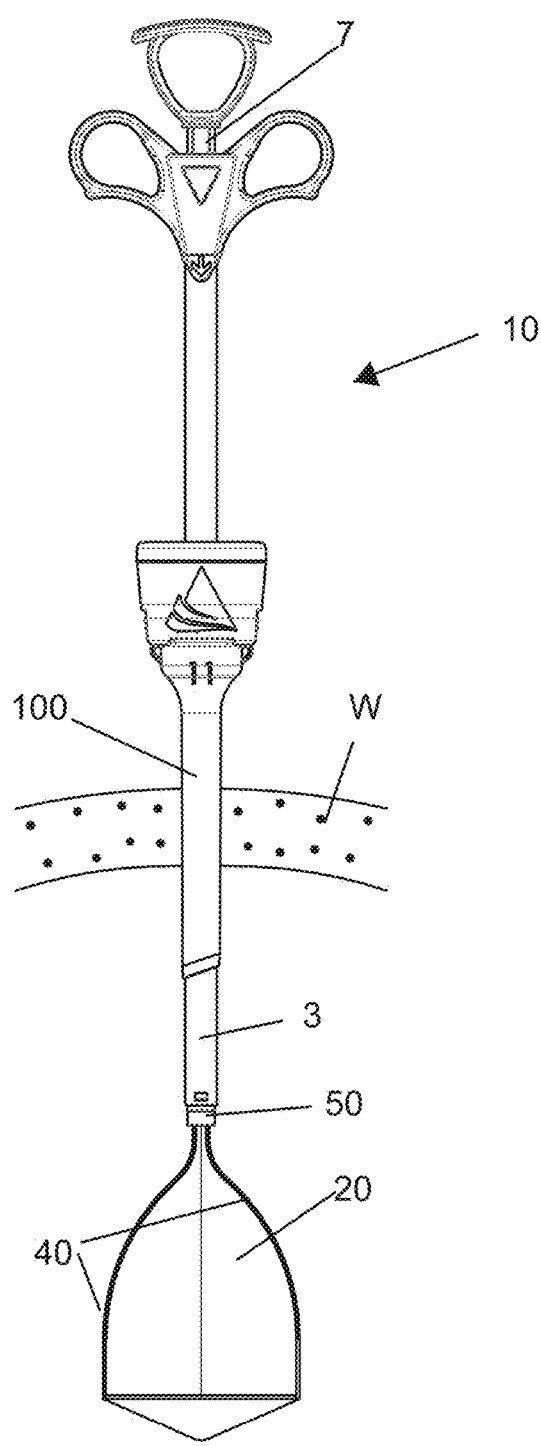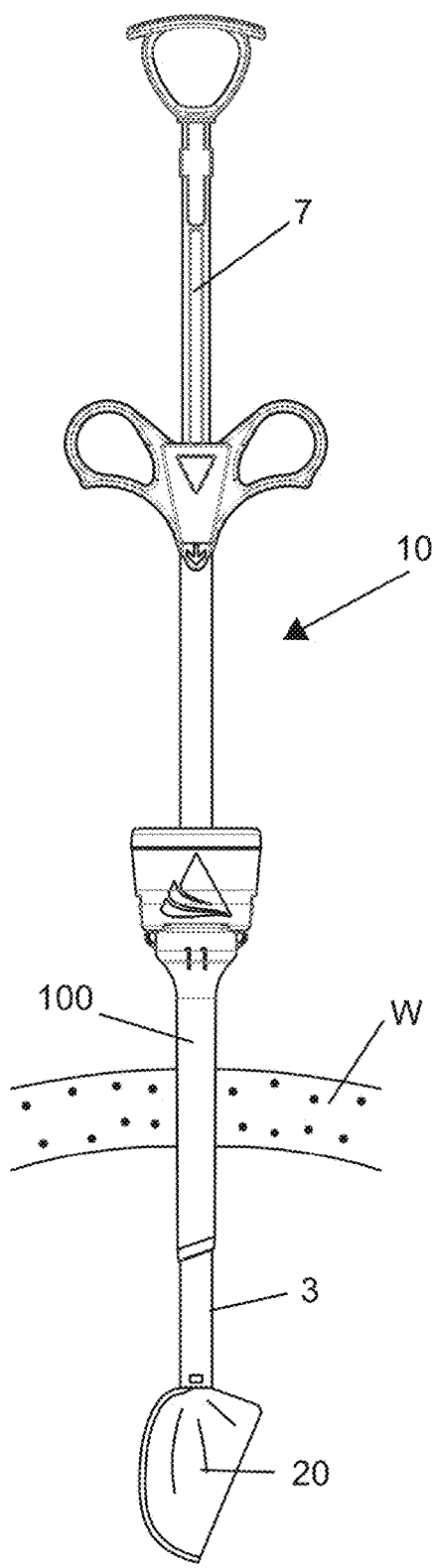
FIG. 3
FIG. 4

REDEPLOYABLE TISSUE RETRIEVAL SYSTEM

CROSS-REFERENCE TO RELATED APPLICATIONS

This application claims priority to and benefit of U.S. Provisional Patent Application Ser. No. 62/936,128 entitled "Redeployable Tissue Retrieval System" filed on Nov. 15, 2019, which is incorporated herein by reference in its entirety.

BACKGROUND OF THE INVENTION

Field of the Invention

The present application relates generally to apparatuses and methods for capturing and retrieving tissue from body cavities and in particular to a specimen retrieval bag device.

Description of the Related Art

Laparoscopic surgery is typically performed through trocars, which provide access across the abdominal wall and into the abdominal cavity. In some surgeries, tissue disposed within the abdominal cavity is cut and removed from the body. However, removal of such tissue from the body may prove difficult due to the limited confines inherent with laparoscopic surgery and the available laparoscopic surgical instruments. For example, to reduce the invasiveness to a patient, it can be desirable to introduce all of the surgical instruments through a single laparoscopic port having a relatively small size. Also, removed tissue may include an infected or cancerous mass or organ, as well as blood, bile and other liquids, all referred to herein as tissue, which may pose infection issues or other complications if left within the body.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity.

In certain procedures it can be desirable to remove multiple tissue specimens from a body cavity in a single procedure for further analysis. For example, for patients undergoing treatment for cancer, serial removal of lymph nodes is a common practice to determine the extent of the spread of the cancer or the reemergence of cancer within the patient. In order to ensure proper identification of the lymph nodes from a specific area of the body, it can be important to remove the lymph nodes in series, sometimes one at a time, from the patient to ensure an accurate determination of the stage of the cancer. Surgeons typically start with extraction of the sentinel lymph node, the lymph node closest to the tumor, and then proceed to other lymph nodes in the surrounding area. In some procedures, each lymph node that is removed from the patient is immediately analyzed for the presence of cancer by a pathologist during the surgery prior to the removal of the next lymph node to minimize the number of lymph nodes removed from the patient. Thus, it can be desirable that a tissue retrieval device be redeployable to obtain multiple tissue specimens in a single procedure.

SUMMARY OF THE INVENTION

In certain embodiments, a tissue retrieval system is provided. The tissue retrieval system comprises a tubular introducer, an actuator, a retaining latch, a pair of support arms, a bead, and a tissue retrieval bag. The tubular introducer has a proximal end and a distal end and a lumen extending between the proximal end and the distal end. The actuator is longitudinally slidable within the lumen of the introducer. The actuator has a proximal end and a distal end. The retaining latch is positioned at the distal end of the actuator. The pair of support arms extend from the distal end of the actuator. The bead is positioned distal the retaining latch. The bead is releasably coupled to the retaining latch. The tissue retrieval bag is coupled to the bead and removably coupled to the support arms.

In certain embodiments, a tissue retrieval system is provided herein. The tissue retrieval system comprises a tubular introducer, a handle assembly, an actuator, and a tissue retrieval bag. The tubular introducer has a proximal end and a distal end and a lumen extending between the proximal end and the distal end. The handle assembly is positioned at the proximal end of the introducer. The actuator is longitudinally slidable within the lumen of the introducer. The actuator has a proximal end and a distal end. The tissue retrieval bag is releasably coupled to the distal end of the actuator. The handle assembly comprises a proximal stop mechanism and a distal stop mechanism such that the actuator is repeatably longitudinally slidable between a proximal position in which the tissue retrieval bag is withdrawn into the distal end of the introducer and a first deployed position in which the tissue retrieval bag is deployed from the distal end of the introducer and coupled to the actuator.

BRIEF DESCRIPTION OF THE DRAWINGS

FIG. 3 is a top view of the tissue retrieval system of FIG. 1A positioned through an access port in a surgical site with the tissue retrieval bag in a deployed configuration;

FIG. 4 is a top view of the tissue retrieval system of FIG. 1A positioned through an access port in a surgical site with the tissue retrieval bag in a redeployable cinched configuration;

DETAILED DESCRIPTION OF THE INVENTION

Figure 1A:
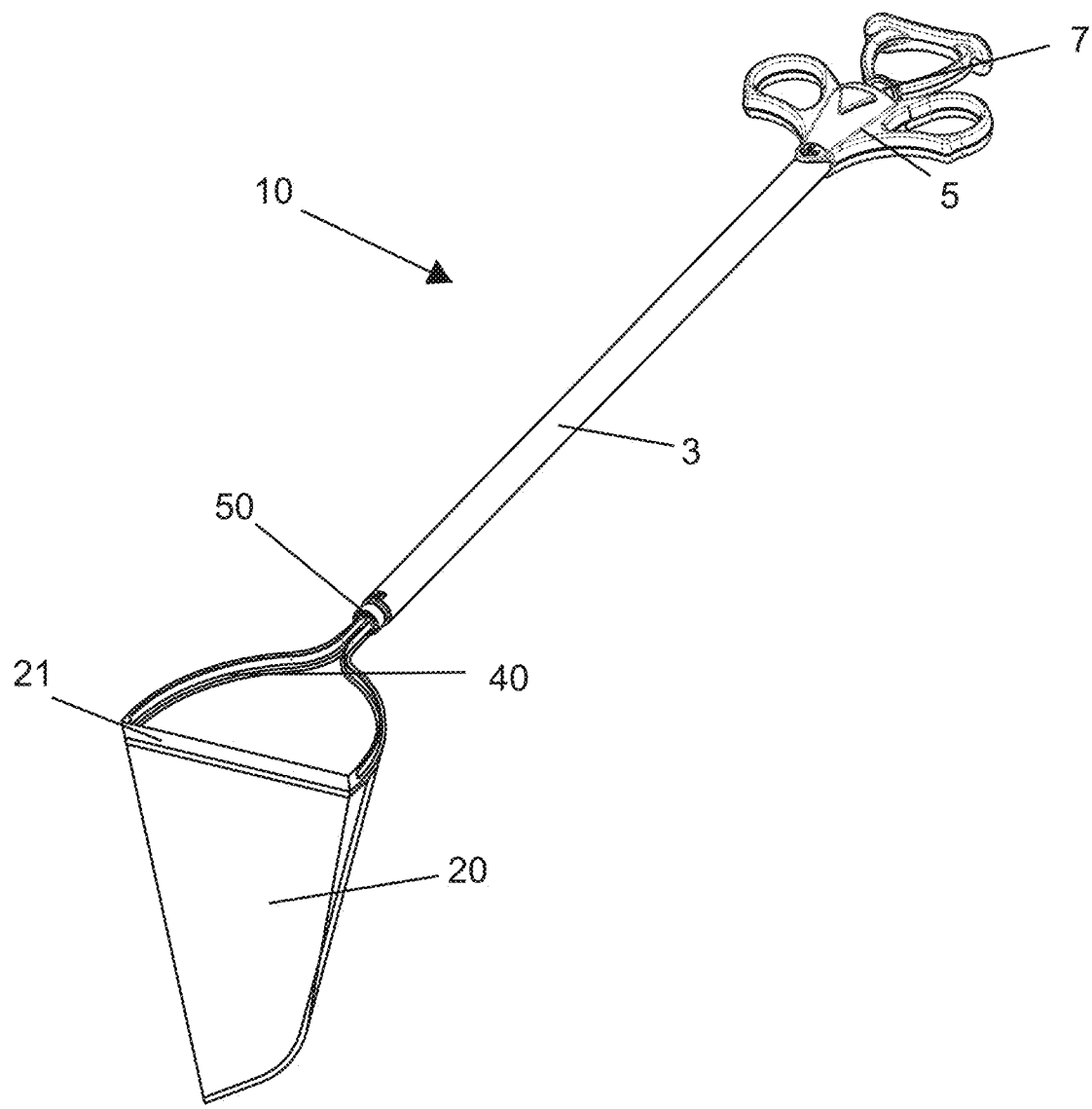
FIG. 1A is a perspective view of an embodiment of tissue retrieval system with an embodiment of tissue retrieval bag in a first deployed configuration.
Figure 1B:
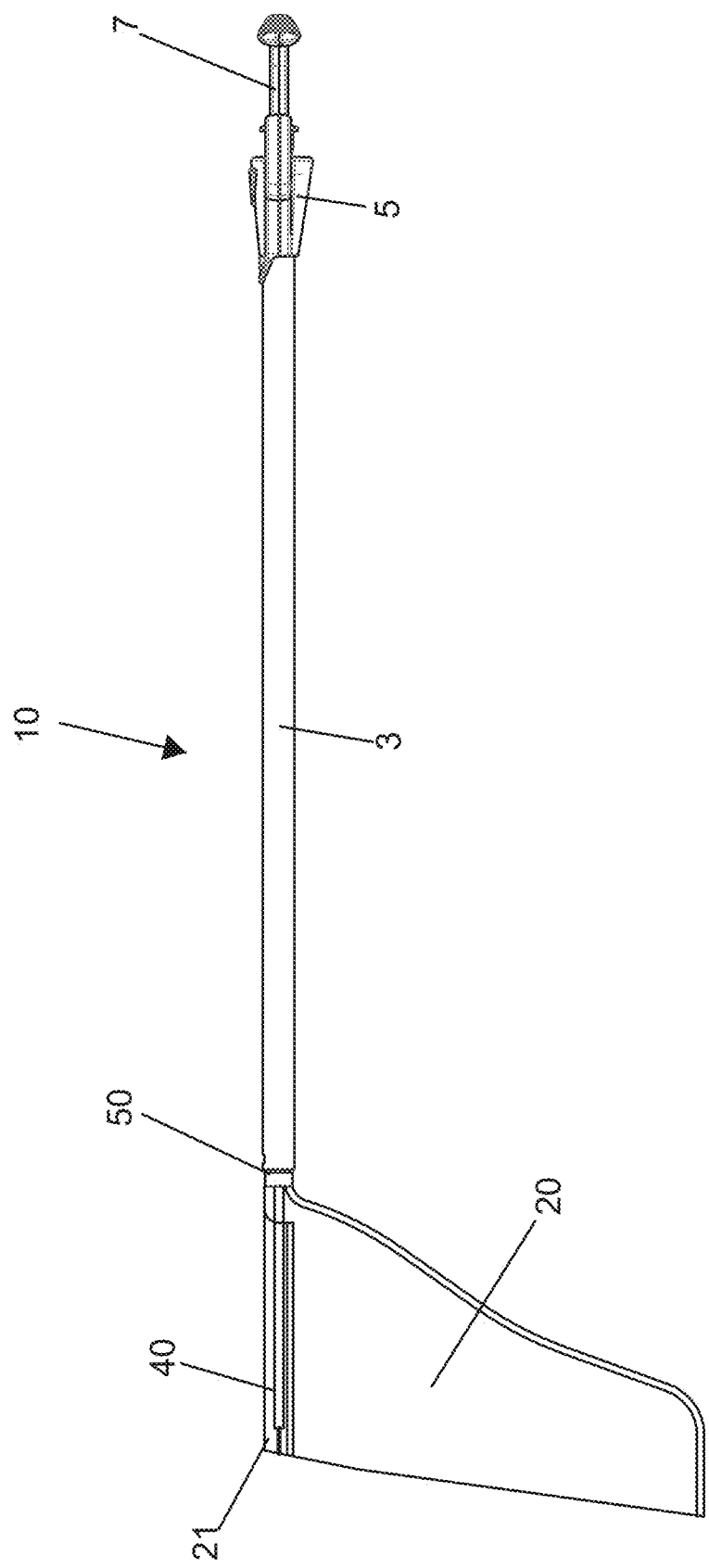
FIG. 1B is a side view of the tissue retrieval system of FIG. 1A.

With reference to FIGS. 1A and 1B, an embodiment of tissue retrieval system 10 is illustrated. The illustrated tissue retrieval system can be used for containing and withdrawing excised tissue specimens from within a body cavity. Certain aspects of tissue retrieval systems are described in U.S. Pat. No. 8,721,658, entitled "TISSUE RETRIEVAL SYSTEM," and U.S. Pat. No. 9,033,995, entitled "SINGLE INCISION LAPAROSCOPIC TISSUE RETRIEVAL SYSTEM." Each of these patents is incorporated by reference herein in its entirety.

In various embodiments, tissue retrieval systems 10 described herein provide a versatile redeployable retrieval system that can be used for serially containing and withdrawing multiple small tissue specimens during a surgical procedure without removing the retrieval bag from the device while also enabling the extraction of a large tissue specimen by cinching the retrieval bag and then detaching the retrieval bag from the introducer. In some procedures, the surgeon may only need the ability to serially contain and withdraw small specimens from the patient. In some procedures, the surgeon may need the ability to serially contain and withdraw multiple small tissue specimens and may then also need to contain and extract a large specimen. In other procedures, the surgeon may only need to contain and extract a large tissue specimen. As the retrieval systems described herein meet many different surgical requirements, a hospital or surgery center using these systems may be able to limit the number of retrieval system models to stock for its surgical needs.

The illustrated tissue retrieval system can desirably be used in certain procedures for serially containing and withdrawing multiple excised small tissue specimens. Advantageously, certain embodiments of tissue retrieval system described herein can permit the use of a single retrieval system for the serial removal of multiple lymph nodes during a procedure.

With reference to FIGS. 1A and 1B, in certain embodiments, a tissue retrieval system 10 includes a retrieval bag 20 at its distal end, which provides a receptacle for tissue specimens. The retrieval bag 20 can have an open end and a closed end opposite the open end. The retrieval bag 20 can further comprise a cuff 21 formed at the open end for receiving a pair of support arms 40 to suspend the retrieval bag 20 and a cord loop to selectively cinch the open end of the retrieval bag. In various embodiments, the retrieval bag can be formed of a ripstop nylon and polyurethane laminate, polyurethane, or a combination of both materials. For example, the retrieval bag can be formed from a ripstop nylon and polyurethane laminate and can include a polyurethane reinforcement at the tip of the retrieval bag to increase the burst strength and puncture resistance of the retrieval bag. The reinforcement can be comprised of a ripstop nylon or a ripstop nylon and polyurethane laminate. As an alternative to the ripstop nylon and polyurethane laminate, the ripstop nylon can be coated with polyurethane.

In a procedure to retrieve multiple small specimens, after insertion of a tissue specimen into the retrieval bag, the retrieval bag 20 can be reversibly closed to prevent spillage of its contents and to prevent contamination of the body cavity and body cavity wall during withdrawal of the retrieval bag 20 from within the body cavity. Once the retrieval bag is withdrawn from the body cavity, the retrieval bag is reopened, the tissue specimen can be removed, labeled, and then forwarded to a pathologist for analysis. The retrieval bag can then be fully retracted into the introducer tube and redeployed within the patient for subsequent containment and withdrawal of the next targeted tissue specimen.

The tissue retrieval system 10 can also be used in procedures for removing large tissue specimens, such as a gallbladder or kidney, from within a body cavity. In these procedures, the retrieval bag 20 can be fully cinched closed and detached from the system for subsequent withdrawal of the retrieval bag 20 through the body wall. In some procedures, such as those related to the excision of cancerous tissue, it may be desirable to first serially remove small tissue specimens, such as lymph nodes, and to then remove the larger tissue specimen. In this case, the tissue retrieval system 10 enables the retrieval bag to be reversibly closed for serially removing smaller tissue specimens and enables the retrieval bag to be fully cinched closed and detached for removal of the large tissue specimen.

With reference to FIGS. 1A-6A, certain embodiments of tissue retrieval system 10 are illustrated in various configurations for use in procedures to retrieve multiple tissue specimens in a single procedure. With reference to FIGS. 1A and 1B, the tissue retrieval system 10 is illustrated in a first deployed condition. In the illustrated embodiment, the tissue retrieval system has an introducer 3 and an actuator 7 or actuation rod. The introducer 3 in one aspect has a tubular configuration with a hollow lumen and a handle assembly 5 extending from a proximal end of the introducer 3. In some embodiments, the introducer 3 can be sized and configured for placement through a standard-size trocar. For example, it can be desirable that the introducer 3 can be sized as a 5 mm laparoscopic surgical instrument to be introduced through relatively small diameter trocars such as 5-7 mm trocars. In other embodiments, the introducer 3 can be sized as a 10 mm or a 12 mm laparoscopic surgical instrument. In some embodiments, the introducer 3 can have a non-standard size for application at a specific location. In some embodiments, the tissue retrieval system 10 can include a relatively long introducer, such as, for example, a 45 cm long introducer 3 to improve access to the surgical site.

The handle assembly 5 of the illustrated embodiment can comprise a compact handle member that can be adapted for placement adjacent other surgical instruments in a single port laparoscopic surgical site. Thus, in some embodiments, the tissue retrieval system is adapted to be utilized during single incision laparoscopic procedures. In other embodiments, the handle assembly can include a pair of finger loops or grips formed with or otherwise coupled to the handle assembly 5 that can be utilized to hold or stabilize the introducer 3 as desired.

Figure 2:
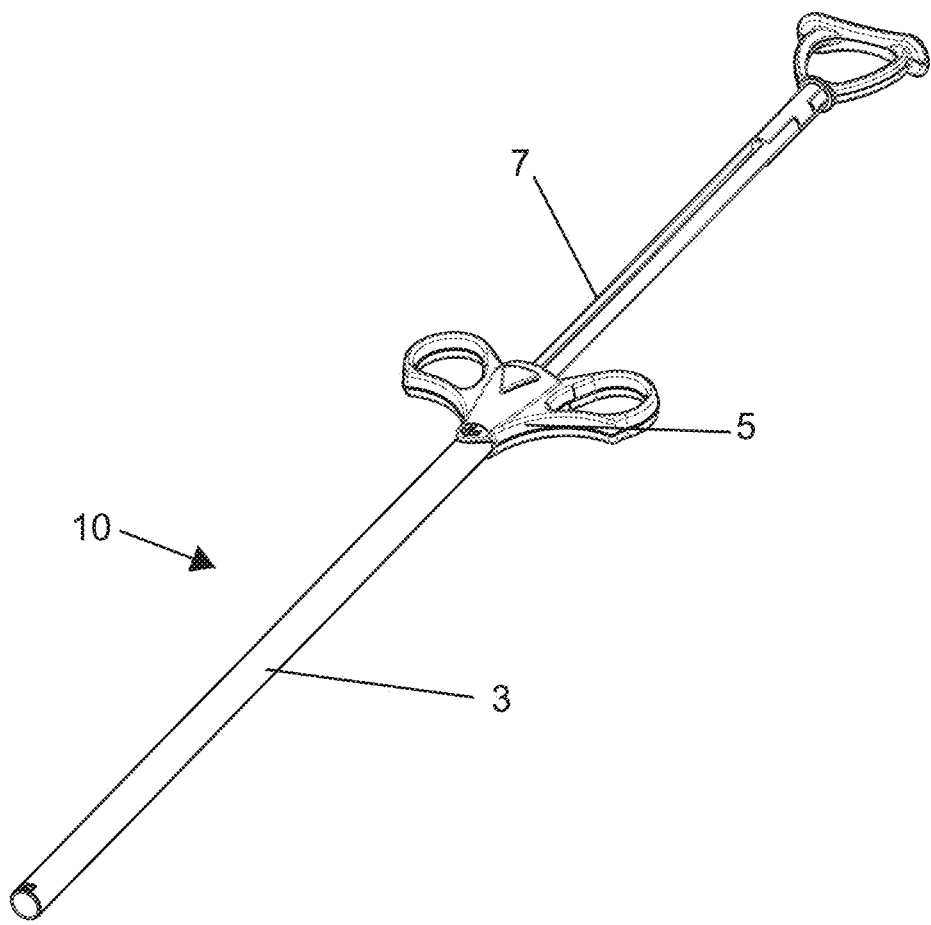
FIG. 2 is a perspective view of an embodiment of tissue retrieval system with an embodiment of tissue retrieval bag in a stowed configuration.

In the illustrated embodiment of tissue retrieval system 10, the introducer 3 has a proximal end and a distal end that are generally open, which can facilitate access to the hollow lumen. As illustrated, the actuator 7 extends into the hollow lumen from the open proximal end thereof, and at least a portion of the actuator 7 is slidably movable within the hollow lumen of the introducer 3. With reference to FIG. 2, the actuator rod can be withdrawn to a proximal position for insertion to a surgical site through an access port such as a trocar. With the actuator 7 in the proximal position the tissue retrieval bag 20 is in a stowed configuration positioned in the hollow lumen of the introducer 3. The actuator 7 in one aspect has a handle such as a thumb loop extending from a proximal end thereof. The handle provides a graspable portion of the device to control or facilitate movement of the actuator 7 relative to the introducer 3 between the proximal position (illustrated in FIG. 2), and a first deployed condition of the tissue retrieval system (illustrated in FIG. 1A).

With reference to FIGS. 3-6A exemplary methods for using the illustrated embodiment of tissue retrieval system 10 to retrieve tissue specimens at a surgical site are illustrated. In certain embodiments, the tissue retrieval system can be provided in either a stowed configuration (FIG. 2) or a first deployed configuration (FIG. 1A). In some embodiments, it can be desirable that the tissue retrieval system 10 is packaged with the retrieval bag 20 deployed out of the distal end of the introducer tube to ensure that the retrieval bag 20 maintains its original configuration and easily unfurls during surgical use. During clinical use, an access device such as a trocar 100 comprising a trocar cannula and trocar seal housing is first placed through a body wall W leaving the trocar cannula disposed across the body wall W. If the tissue retrieval system 10 was provided in a first deployed configuration, a nurse or surgeon configures the tissue retrieval system to a stowed configuration (FIG. 2) by fully retracting the retrieval bag 20 within the introducer 3 tube by withdrawing the actuator 7 in a proximal direction to position the actuator rod in a proximal position. The tissue retrieval system 10 can then be inserted into the trocar seal housing and trocar cannula until the distal end of the introducer 3 tube extends beyond the distal end of the trocar cannula. The retrieval bag 20 is then deployed from within the introducer 3 tube and into the body cavity by advancing the actuator in a distal direction to the first deployed position (FIG. 3).

With continued reference to FIG. 3, once extended into the body cavity, the retrieval bag 20 in the first deployed configuration is suspended and held open by two support arms 40 that extend into a cuff at the open end of the retrieval bag. In the illustrated embodiment, the retrieval bag includes a bead 50 attached to a proximal portion of the cuff through which the support arms 40 extend. In the first deployed position, the illustrated embodiment of tissue retrieval system comprises a retaining latch coupled to a distal end of the actuator 7 and engaged with the bead 50. Advantageously, the retaining latch enables the surgeon to selectively control a release of the retrieval bag 20 from the support arms and the actuator. While in the first deployed position, the retaining latch is engaged with the bead 50 to prevent the release of the retrieval bag 20 relative to the support arms, the retaining latch is releasably attached to the bead 50. When engaged with the bead 50, the retaining latch enables the retrieval bag 20 to be completely retracted into the introducer 3 (FIG. 2) with the actuator 7 withdrawn to a proximal position for subsequent insertion through the trocar. When engaged with the bead 50, the retaining latch also enables the retrieval bag 20 to be partially retracted into the introducer tube (FIG. 4) to a redeployable cinched configuration, allowing reversible closing of the opening of the retrieval bag. Thus sequential, repeated opening and closing of the tissue retrieval bag 20 can be used to contain multiple small tissue specimens in a single procedure for subsequent withdrawal from the patient achieved by repeatedly advancing the actuator to a first deployed position (FIG. 3) and withdrawing the actuator towards the proximal position (FIG. 4) to position the tissue retrieval bag in a redeployable cinched configuration.

With reference to FIG. 4, once a small tissue specimen has been positioned in the retrieval bag, partial retraction and closure of the retrieval bag 20 is achieved by retracting the actuator 7 into the introducer 3 tube until the support arms 40 and the cuff are drawn into the introducer 3 tube, leaving a distal portion of the retrieval bag 20 with contained tissue outside of the introducer 3 tube. Various techniques can then be used to remove the tissue specimen from the surgical site across the body wall. For example, the tissue retrieval system 10 can be withdrawn through the trocar, leaving the trocar disposed across the body wall, or the tissue retrieval system can be directly withdrawn through the body wall after withdrawal of the trocar from the patient. For very small tissue specimens, the entire retrieval bag 20 with the contained specimen can be withdrawn into the introducer tube. In this case, the tissue retrieval system can be withdrawn through the trocar, leaving the trocar disposed across the body wall.

Once the tissue retrieval system 10 has been withdrawn from the surgical site, the actuator 7 can be advanced distally to the first deployed position (FIG. 1A) and the tissue specimen removed for analysis. If further small tissue specimens are desired to be obtained, the actuator 7 can then be withdrawn to the proximal position (FIG. 2) for reintroduction to the surgical site as described above. As further described below with reference to FIGS. 16-28 and 56-58, in certain embodiments, the tissue retrieval system can include stop mechanisms to limit travel of the actuator between the proximal position and the first deployed position until it is desired to separate the tissue retrieval bag 20 from the actuator 7. Advantageously, these stop mechanisms can reduce the potential for an inadvertent full deployment of the tissue retrieval bag before all of the desired tissue specimens have been collected for analysis.

The tissue retrieval system 10 can also be used to in procedures to extract relatively large tissue specimens such as a gallbladder, appendix, or kidney. In these procedures, desirably with the tissue retrieval bag in the first deployed configuration (FIG. 3) during placement of a large tissue specimen such as the gallbladder, the retaining latch prevents inadvertent movement of the retrieval bag relative to the support arms and the actuator. Once a large specimen has been positioned in the tissue retrieval bag, it is desirable to cinch and fully detach the retrieval bag from the introducer, leaving the cinched retrieval bag within the body cavity. If the procedure requires the serial removal of small tissue specimens such as lymph nodes and then requires the removal of a large tissue specimen, the cinching and detachment of the retrieval bag would be completed after the serial removal of the smaller tissue specimens. Once the retrieval bag is cinched closed and detached from the introducer, the surgeon then removes the trocar from the body wall and can then extract the retrieval bag through the body wall.

Figure 5:
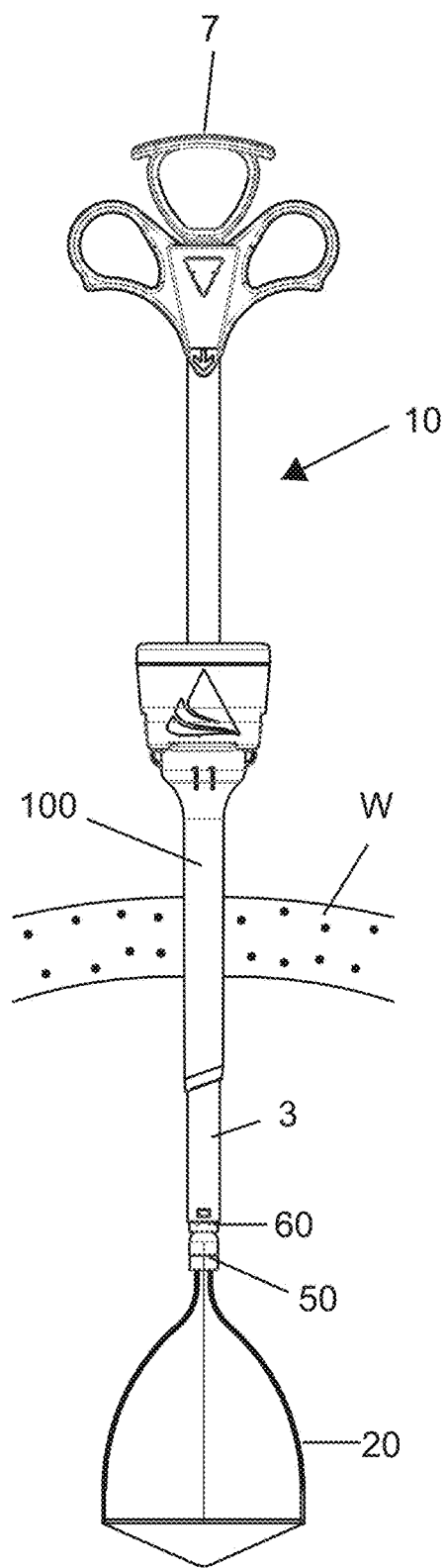
FIG. 5 is a top view of the tissue retrieval system of FIG. 1A positioned through an access port in a surgical site with the tissue retrieval bag in a fully deployed configuration.

In certain embodiments, the tissue retrieval system 10 can be selectively actuated from the first deployed configuration (FIG. 3) to position the actuator and tissue retrieval bag in a fully deployed configuration (FIG. 5). Once a surgeon determines that it is desirable to separate the tissue retrieval bag from the introducer, such as when a large or final tissue specimen is placed within the retrieval bag, the surgeon actuates a deployment release mechanism for example by pressing a deployment release button on the handle assembly. With actuation of the deployment release mechanism, the actuator can be advanced distally beyond the first deployed position to a second or fully deployed position (FIG. 5). Advancement of the actuator to its fully deployed position causes the bead and the distal end of the retaining latch to be disposed out of the distal end of the introducer tube.

Figure 6A:
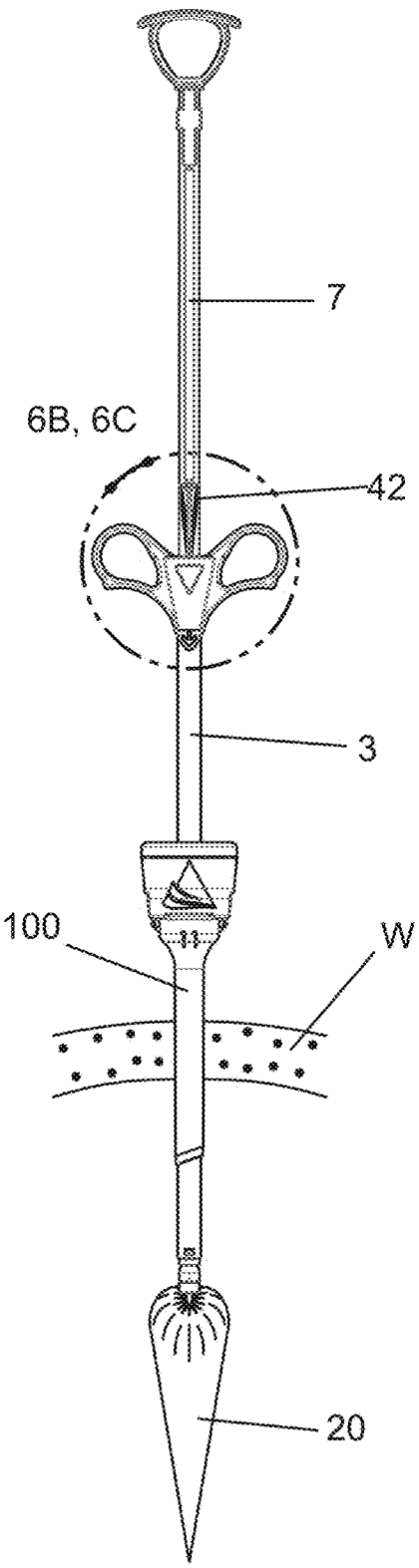
FIG. 6A is a top view of the tissue retrieval system of FIG. 1A positioned through an access port in a surgical site with the tissue retrieval bag in a fully deployed cinched configuration.

With reference to FIGS. 5 and 6A, in certain embodiments, the tissue retrieval system 10 can include a stop mechanism to prevent reintroduction of the bead into the distal end of the introducer 3 once the actuator 7 has been advanced to the fully deployed position. For example, in the illustrated embodiment, the tissue retrieval system 10 comprises a bead stop 60, which is positioned between the actuator 7 and the bead 50. As further discussed below with reference to FIGS. 10-15, with the actuator in the fully deployed position, the bead stop is also advanced to its most distal position where it lockingly engages the introducer to obstruct the distal end of the introducer 3. This obstruction prevents the bead and the retrieval bag, once fully deployed, from being withdrawn into the introducer tube. This obstruction also presents a bearing surface such that subsequent proximal withdrawal of the actuator from the fully deployed position withdraws the support arms from the cuff of the tissue retrieval bag 20 and cinches the tissue retrieval bag 20 (FIG. 6A). Once the retrieval bag is cinched closed, a small loop of the cord loop 42 is exposed near the proximal end of the introducer 3 tube.

In certain embodiments, the tissue retrieval system comprises a cord loop positioned to selectively cinch the opening of the tissue retrieval bag into a closed configuration. The cord loop can extend through the cuff at the open end of the tissue retrieval bag 20 and extend proximally into the introducer along a receiving channel in the actuator. The cord loop can be removably coupled to the actuator. In certain embodiments, the cord loop is dimensioned such that its proximal end is positioned between the proximal end and the distal end of the actuator and retained by the actuator. Desirably, in certain embodiments, the cord loop is dimensioned such that its length enables cinching of the retrieval bag and exposure of the cord loop on the actuator after cinching. When the retrieval bag is cinched closed, the cord loop is fully tensioned. Prior to full tensioning of the cord loop during cinching of the retrieval bag, the cord loop is fully contained within the introducer tube of the retrieval system. In certain embodiments, the cord loop is not exposed during deployment of the retrieval bag or during retraction of the retrieval bag within the introducer tube. For example, during insertion to the surgical site and serial containment and withdrawal of multiple small tissue specimens (FIGS. 2-4), the cord loop is not exposed. In these embodiments, the cord loop 42 is only exposed to the surgeon when the cord loop is fully tensioned and the retrieval bag is cinched closed (FIG. 6A). This feature prevents the surgeon from unintentionally grasping, cutting, releasing, or tensioning the cord loop during use of the device. The cord loop can be stored in the introducer tube in a non-tensioned condition with a portion of the cord loop being folded and stored in a receiving channel on the underside of the actuator.

The cord loop 42 can provide an ergonomic and high strength means for grasping and withdrawing the retrieval bag through the abdominal wall. As the cord is formed of a single loop of cord, there is no limitation in terms of being able to manually grip the cord loop. The cord loop also provides a robust means for withdrawing the retrieval bag through the body wall as two strands of the cord absorb the tension being applied by the surgeon. For example, if the surgeon is applying a tensile force of 20 lbs. to the cord loop during withdrawal of the retrieval bag, each strand of the cord is being tensioned at a force of 10 lbs. Certain other retrieval systems have included relatively small loops of material which can make it difficult to manually grasp the loop. Other retrieval systems have also included a small loop that is connected to a single strand of cord or line where a 20 lb. tensile force applied by the surgeon results in a 20 lb. tensile force being applied to the cord. In some cases, the single strand of cord or line of these other retrieval systems can fail during withdrawal of the retrieval bag.

Another advantage provided by the cord loop is that the cord loop is relatively short after cinching of the retrieval bag, providing for easier management of the cord and easier withdrawal of the retrieval bag through the body wall. In certain embodiments of tissue retrieval systems described herein, the length of the cord loop with the retrieval bag cinched is about 14". Other retrieval systems can have a cord with a length greater than about 25" after cinching of the retrieval bag making the cord unwieldy and difficult to manage and use during withdrawal of the retrieval bag through the body wall.

Figure 6B:
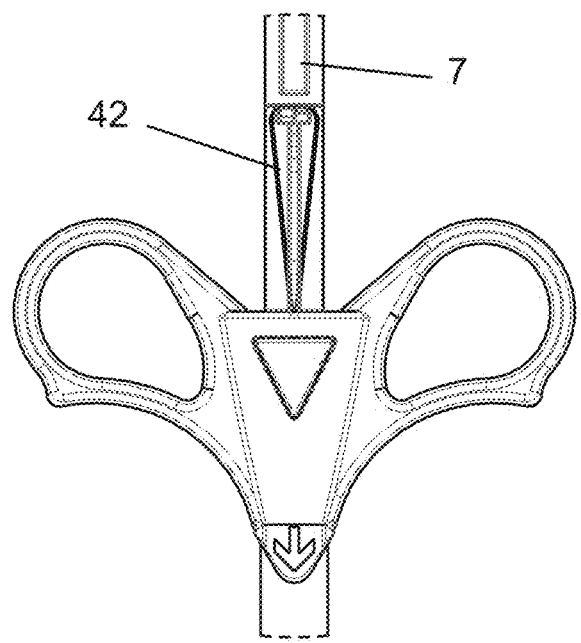
FIG. 6B is a detail view of the tissue retrieval system of FIG. 1A positioned through an access port in a surgical site with the tissue retrieval bag in a fully deployed cinched configuration with an embodiment of cord loop.
Figure 6C:
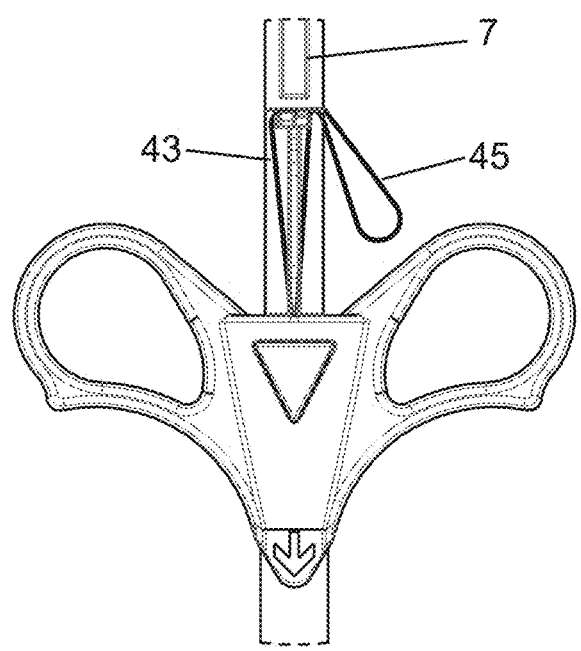
FIG. 6C is a detail view of the tissue retrieval system of FIG. 1A positioned through an access port in a surgical site with the tissue retrieval bag in a fully deployed cinched configuration with another embodiment of cord loop.

With reference to FIG. 6A-6C, once the tissue retrieval bag 20 has been cinched, there are at least two techniques for withdrawal of the cinched retrieval bag from within the body cavity. For the first method, the retrieval bag can be completely detached and removed from the actuator and introducer tube by lifting the cord loop 42 from the retaining slot on the actuator. FIG. 6B is a detail view of a cord loop coupled to the actuator once the tissue retrieval bag has been cinched. In FIG. 6B, the cord loop 42 comprises a single continuous loop. FIG. 6C illustrates a detail view of another embodiment of cord loop 43 that can be used in various embodiments of tissue retrieval systems described herein. In the illustrated embodiment, the cord loop 43 can comprise a grasping loop 45 at a proximal end thereof adjacent the retaining slot on the actuator. Advantageously, the grasping loop 45 can facilitate grasping of the cord loop 43 once the tissue retrieval bag has been cinched. In certain embodiments, the grasping loop 45 can be coupled to the cord loop 43 at a low profile interface such as by ultrasonic welding, bonding, heat sealing or fusing together. Such a low profile interface can desirably facilitate assembly of the cord loop with the actuator in the tissue retrieval system as the cord loop may be routed to pass through one or more sealing O-rings or other constrictions within the introducer, which may impede the passage of a knot or other higher profile coupling.

With reference to FIG. 6A, once the cord loop has been decoupled from the actuator, the device and the trocar seal and cannula can then be withdrawn from the body wall leaving the retrieval bag 20 in the body cavity and the cord loop 42 disposed across the body wall. The neck of the retrieval bag can then be withdrawn through the body wall using the bead as a dilator to aid with movement of the retrieval bag through the layers of tissue fibers in the body wall. Once the neck of the retrieval bag has traversed the body wall, the retrieval bag can then be reopened by manually grasping the closed end of the retrieval bag and the bead and sliding the bead along the cord. The retrieval bag can then be accessed to remove or compact its contents to aid with complete withdrawal from the body cavity using standard open and laparoscopic instrumentation such as forceps, graspers, and aspiration probes. Once the bulk of the contents are removed, the retrieval bag can then be closed by manually grasping the open end of the retrieval bag and the bead and sliding the bead along the cord. The cord loop can then be grasped manually and the retrieval bag then completely withdrawn from the body cavity. In some procedures, the surgeon may withdraw the retrieval bag through the body wall without reopening the retrieval bag.

A second method for withdrawal of the retrieval bag 20 from within the body cavity can be used for smaller tissue specimens, such as a small gallbladder, placed in the retrieval bag which are not likely to need to be aspirated, compacted, or removed from the retrieval bag prior to withdrawal of the retrieval bag through the body wall. In this case, the cord loop can be left attached to the actuator and the entire device along with the trocar seal and cannula can be simultaneously withdrawn from the body cavity and through the body wall.

Figure 7:
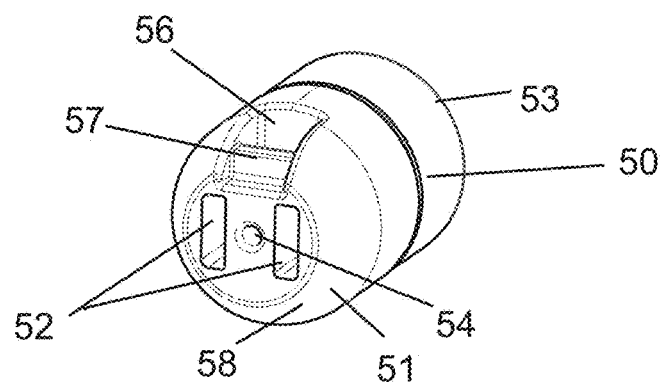
FIG. 7 is a perspective view of an embodiment of bead for the tissue retrieval system of FIG. 1A.
Figure 8:
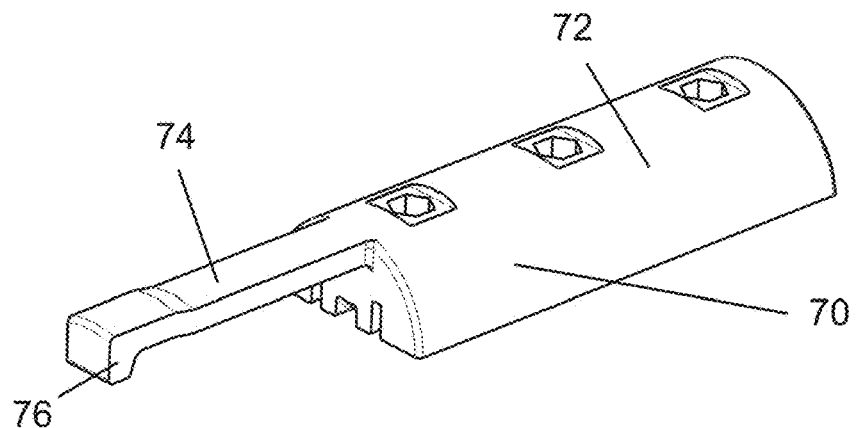
FIG. 8 is a perspective view of an embodiment of retaining latch for the tissue retrieval system of FIG. 1A.
Figure 9:
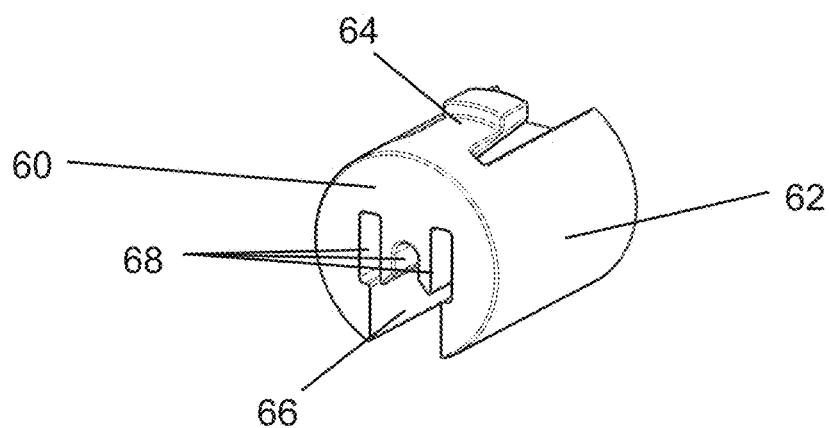
FIG. 9 is a perspective view of an embodiment of bead stop for the tissue retrieval system of FIG. 1A.

With reference to FIGS. 7-9, certain components of the tissue retrieval systems described herein that contribute to the redeployable operation of these systems are illustrated. The operation of these components at a distal end of an introducer in an embodiment of tissue retrieval system is illustrated in the first deployed position in FIGS. 10 and 11 and in a second deployed position in FIGS. 12-15. FIG. 7 illustrates an embodiment of bead for use with various embodiments of tissue retrieval system. FIG. 8 illustrates an embodiment of retention latch for use with various embodiments of tissue retrieval system. FIG. 9 illustrates an embodiment of bead stop for use with various embodiments of tissue retrieval system.

With reference to FIG. 7, an embodiment of bead 50 for a tissue retrieval system is illustrated. As illustrated, the bead 50 comprises a pair of channels 52 through which the support arms can slide. The bead 50 can further comprise a hole 54 through which the cord loop runs that frictionally engages the cord loop to enable the retrieval bag to be cinched closed and reopened as needed once the retrieval bag has been completely detached from the actuator and the introducer. The bead can also be configured to releasably engage the retaining latch. In the illustrated embodiment, the bead 50 includes a recess 56 and a ledge 57 positioned in the recess to engage a distal end of the retaining latch. In certain embodiments, the bead 50 is injection molded from polycarbonate, and, in other embodiments, the bead 50 can be formed from other materials such as nylon, ABS, and polyester.

With continued reference to FIG. 7, in certain embodiments, the bead 54 is configured to facilitate withdrawal of the cinched retrieval bag through the body wall. In certain embodiments a proximal end of the bead 54 can comprise a blunt, tapered, or radiused surface 58 to facilitate withdrawal of the bead through a body wall. Thus, the bead can dilate muscle and tissue fibers of the body wall during withdrawal of the retrieval bag. Advantageously, as the bead traverses the body wall, the cinched cuff and the remainder of the retrieval bag can easily follow. Retrieval systems that do not include a bead can require the bunched cuff of the cinched retrieval bag to be pulled directly into the body wall where the bunched cuff can sometimes catch on the body wall resulting in an increase in the extraction force during withdrawal of the retrieval bag.

With continued reference to FIG. 7, the illustrated embodiment of bead 50 includes a passage, bore, or hole 54 through which the cord loop runs that frictionally engages the cord loop to enable the retrieval bag to be cinched closed and reopened as needed once the retrieval bag has been detached from the introducer. Thus, during withdrawal of the retrieval bag from the body cavity, once the neck of the retrieval bag has traversed the body wall, the retrieval bag can advantageously be easily reopened to enable access to remove or compact its contents. Previous retrieval bags with no bead can be very difficult or impossible to reopen once the retrieval bag has been cinched closed.

Figure 11:
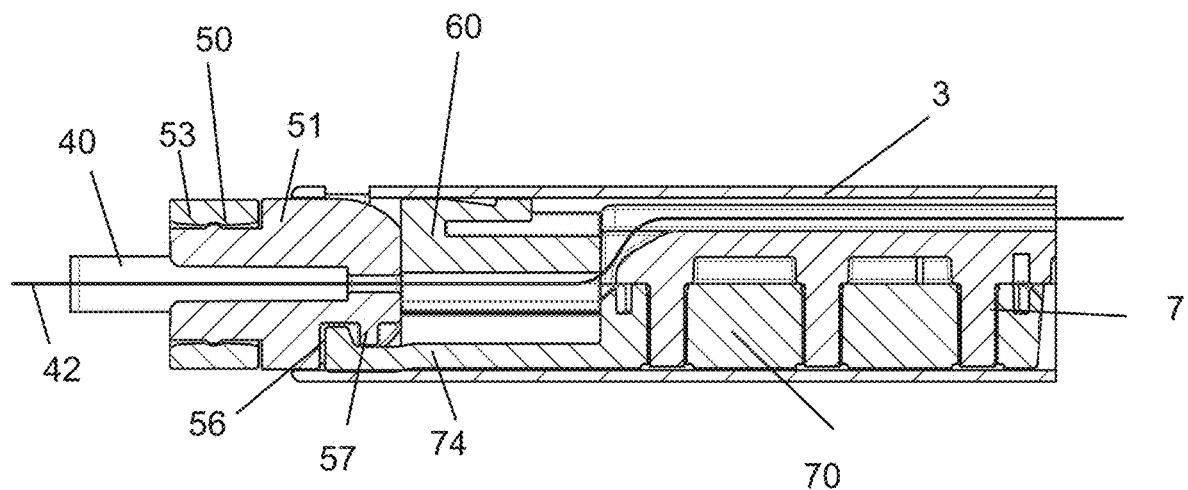
FIG. 11 is a cross-sectional side view of the bead, retaining latch, and bead stop of the tissue retrieval system of FIG. 1A with the tissue retrieval bag in a first deployed configuration.

With continued reference to FIG. 7, in certain embodiments the bead 50 can comprise a two-piece assembly comprising a bead body 51 and an annular clamp 53 positioned around a portion of the bead body (FIG. 11). A portion of the tissue retrieval bag can be positioned between the bead body 51 and the clamp 53 to couple the tissue retrieval bag to the bead 50. Various joining techniques such as gluing with chemical adhesives, ultrasonic welding, heat sealing, or other chemical, thermal, or mechanical joining processes can further secure the retrieval bag to the bead body and/or clamp. In other embodiments, the bead can be a single component without an encircling clamp, and the single component bead can be coupled to the retrieval bag with various chemical, thermal, or mechanical joining processes.

With reference to FIG. 8, an embodiment of retaining latch 70 for use in various embodiments of tissue retrieval system is illustrated. The illustrated retaining latch 70 comprises an actuator cap configured to be positioned at the distal end of the actuator. Thus, the retaining latch 70 can comprise a proximal portion 72 coupled with the distal end of the actuator. The retaining latch comprises a latch arm 74 extending distally from the proximal portion 72. The latch arm 74 can be configured to releasably engage the bead. For example, in the illustrated embodiment, the latch arm 74 comprises a latch tab 76 at the distal end thereof. In the illustrated embodiment, the latch tab 76 extends radially inwardly to releasably engage the ledge 57 of the bead 50 (FIG. 7). In certain embodiments, the actuator cap with the integral retaining latch is injection molded from polycarbonate, and, in other embodiments can be formed from other materials such as nylon, acrylonitrile butadiene styrene (ABS), polyester, polypropylene, stainless steel, spring steel, titanium, or nitinol.

While in the illustrated embodiment, the actuator cap comprises a single retaining latch engageable with a corresponding ledge on the bead, it is contemplated that in other embodiments the actuator cap includes two retaining latches engageable with the bead, and the bead comprises a corresponding two ledges. Moreover, while the actuator cap and retaining latch are illustrated as a single component, it is contemplated that in other embodiments, the actuator cap is formed of two components where the body of the actuator cap is formed of a polymer material such as polycarbonate, ABS, nylon, or polypropylene, and the retaining latch is formed of a metal material such as stainless steel, spring steel, titanium, or nitinol. In certain embodiments, the metal retaining latch can be overmolded during molding of the actuator cap, bonded to the actuator cap, heat staked to the actuator cap, snap fitted to the actuator cap, mechanically trapped between the actuator cap and the introducer tube, or mechanically trapped between the actuator cap and the actuator. The metal retaining latch can be biased to spring to a decoupled position upon advancement of the actuator to its fully deployed position. The separate retaining latch can include a spring or an integral spring element to bias the latch to a decoupled position relative to the ledge on the bead.

With reference to FIG. 9, an embodiment of bead stop 60 for use in various embodiments of tissue retrieval system is illustrated. In the illustrated embodiment, the bead stop 60 comprises a body portion 62 and a locking arm 64. As illustrated, the locking arm 64 is integrally formed with the body portion 62 and is formed as a cantilever spring arm. The locking arm 64 can comprise a tab configured to engage the introducer. The body portion 62 can be configured to be positioned between the distal end of the actuator of the tissue retrieval system and the bead of the tissue retrieval bag. Accordingly, the body portion 62 of the bead stop can comprise a channel 66 through which the latch arm 74 of the retaining latch 70 (FIG. 8) can pass, and one or more passages 68 through which the support arms coupled to the actuator and cord loop of the tissue retrieval bag can pass.

When the actuator is in the proximal or first deployed positions (FIG. 2 and FIG. 1A), the cantilever spring arm of the bead stop is in a deflected state within the introducer tube. When the retrieval bag is advanced to its fully deployed position, the cantilever spring arm springs radially outward to engage and lock into a mating slot on the introducer tube. It is contemplated that the retrieval system can be packaged and stored with the actuator in its first deployed position with the retrieval bag deployed. Thus, with the actuator in this position, the cantilever spring arm on the bead stop is subjected to a constant flexural deflection force during storage of the device. For this reason, in certain embodiments, the bead is preferably formed from a high heat polymer material with a high resistance to creep such as polyetherimide (PEI), polyphenylsulfone (PPSU), or polyetheretherketone (PEEK). In other embodiments, the bead stop can also be formed from stainless steel, spring steel, nitinol, or other metal materials. In certain embodiments, the bead stop could also be formed of a combination of materials such as a polymer body formed from polycarbonate, ABS, nylon, or polyester with a stainless steel spring arm. The stainless steel spring arm can be overmolded during molding of the bead stop, bonded to the bead stop, heat staked to the bead stop, or snap fitted to the bead stop.

While the illustrated embodiment of bead stop comprises a cantilever spring arm having a generally rectangular prismatic tab configured to engage a generally rectangular slot in the introducer tube, it is contemplated that in other embodiments, the bead stop can comprise a generally cylindrical protrusion on the cantilever spring arm to mate with a circular aperture in the introducer tube. Moreover, while the illustrated bead stop includes a single cantilever spring arm, in other embodiments, the bead stop includes two or more cantilever spring arms engageable with a corresponding two or more slots or apertures in the introducer tube.

Figure 10:
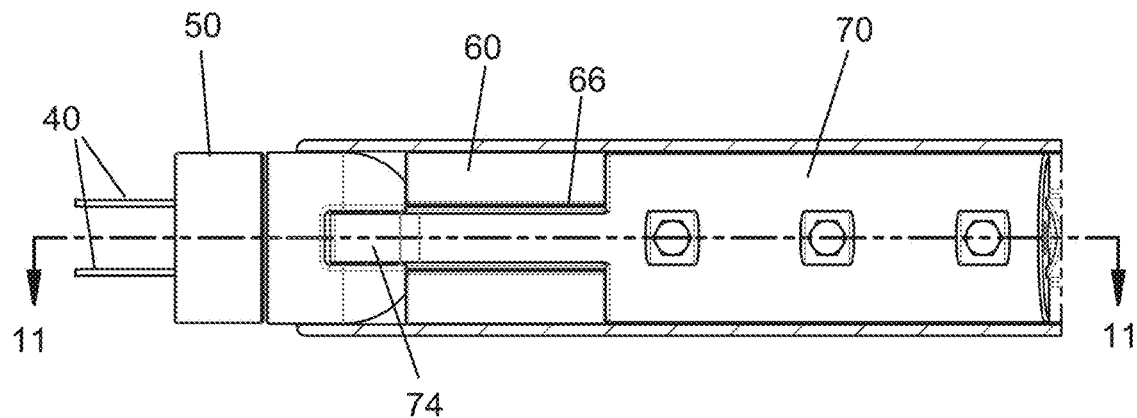
FIG. 10 is a partial cut away bottom view of the bead, retaining latch, and bead stop of the tissue retrieval system of FIG. 1A with the tissue retrieval bag in a first deployed configuration.

With reference to FIGS. 10 and 11, arrangement of the bead 50, bead stop 60, and retaining latch 70 at the distal end of the introducer 3 with the actuator 7 advanced to a first deployed position (corresponding to a tissue retrieval system positioned as illustrated in FIG. 3) are illustrated. A position of the support arms 40 and cord loop 42 with the actuator 7 in the first deployed position is also illustrated. In the first deployed position, latch arm 74 of the retaining latch 70 extends distally from the distal end of the actuator cap and through the channel 66 of the bead stop 60. The latch tab 76 at the distal end of the latch arm, 74 is positioned into a recess 56 on the bead 50 where it engages with the ledge 57 on the bead. With the retaining latch 70 coupled to the bead 50, the retaining latch is in a non-deflected state. When the actuator 7 is advanced to the first deployed position, its initial position for redeployable use of the retrieval bag, the retaining latch 70 and the proximal portion of the bead 50, which includes the recess 56 and the ledge 57, are contained within the introducer 3 tube. With the retaining latch 70 and the proximal portion of the bead 50 contained within the introducer 3 tube, it is not possible for the retaining latch 70 to uncouple from the bead 50 as there is not sufficient clearance between the ledge 57 on the bead 50 and the inside diameter of the introducer tube for the retaining latch 70 to ride over the ledge 57 on the bead 50 and decouple from the bead. Therefore, with the actuator 7 in its first deployed position, the retaining latch 70 serves to enable the retrieval bag to be retracted within the introducer tube as the actuator 7 is pulled in a proximal direction.

Figure 12:
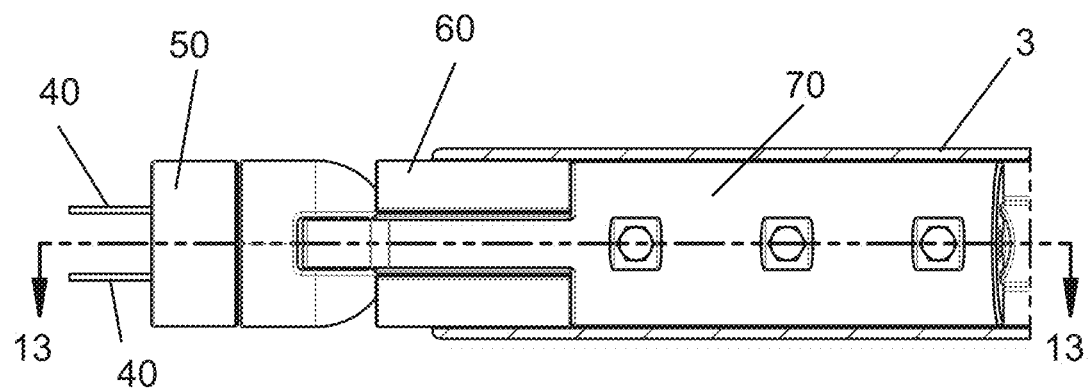
FIG. 12 is a partial cut away bottom view of the guide bead, retaining latch, and bead stop of the tissue retrieval system of FIG. 1A with the tissue retrieval bag in a fully deployed configuration.
Figure 13:
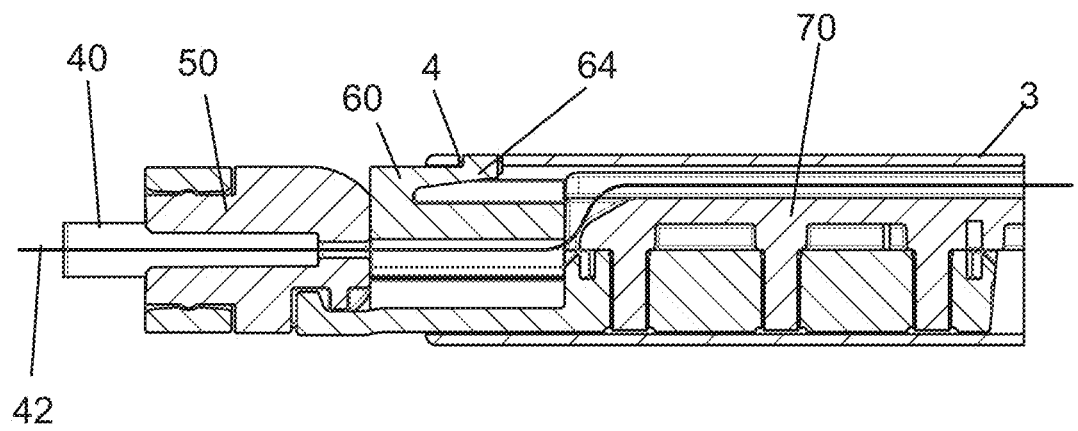
FIG. 13 is a cross-sectional side view of the guide bead, retaining latch, and bead stop of the tissue retrieval system of FIG. 1A with the tissue retrieval bag in a fully deployed configuration.

With reference to FIGS. 12 and 13, arrangement of the bead 50, bead stop 60, and retaining latch 70 at the distal end of the introducer 3 with the actuator 7 advanced to a second, fully deployed position (corresponding to a tissue retrieval system positioned as illustrated in FIG. 5) are illustrated. A position of the support arms 40 and cord loop 42 with the actuator in the second deployed position is also illustrated. When the actuator is advanced to its fully deployed position, a proximal portion of the bead 50 and the attached retaining latch 70 are advanced out of the distal end of the introducer 3 tube. The bead stop 60 is also advanced distally to a position where its locking arm 64 or integral cantilever spring arm springs upward and locks into a rectangular mating slot 4 on the introducer 3 tube. With the bead stop 60 locked into the distal end of the introducer 3 tube, the bead stop 60 will prevent the bead and the retrieval bag from being withdrawn into the introducer tube.

Figure 14:
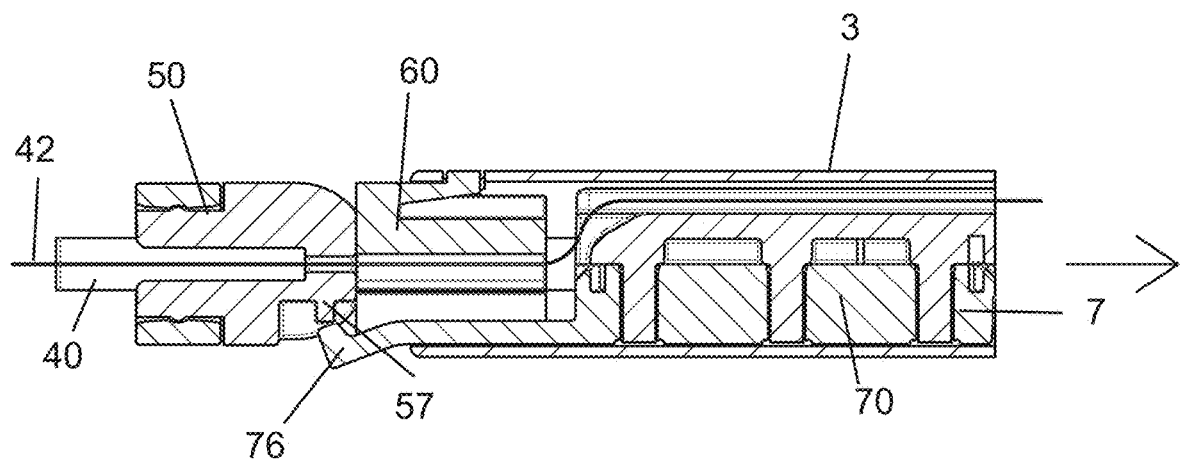
FIG. 14 is a cross-sectional side view of the guide bead, retaining latch, and bead stop of the tissue retrieval system of FIG. 1A with the tissue retrieval bag in a fully deployed configuration and the retaining latch decoupling from the guide bead as an actuator is retracted.
Figure 15:
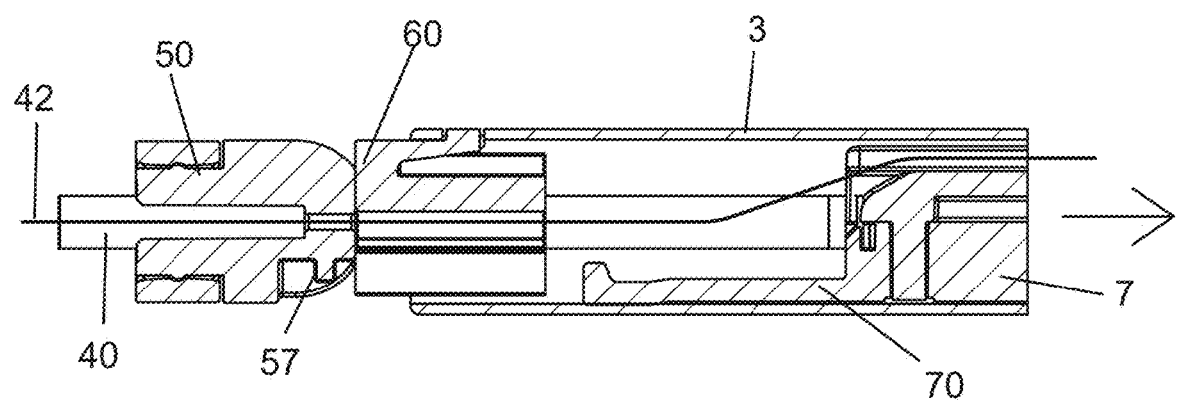
FIG. 15 is a cross-sectional side view of the guide bead, retaining latch, and bead stop of the tissue retrieval system of FIG. 1A with the tissue retrieval bag in a fully deployed configuration and the retaining latch fully decoupled from the guide bead as an actuator is retracted.
Figure 16:
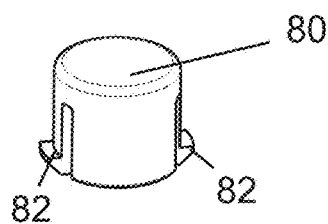
FIG. 16 is a perspective view of an actuator post of the tissue retrieval system of FIG. 1A.
Figure 17:
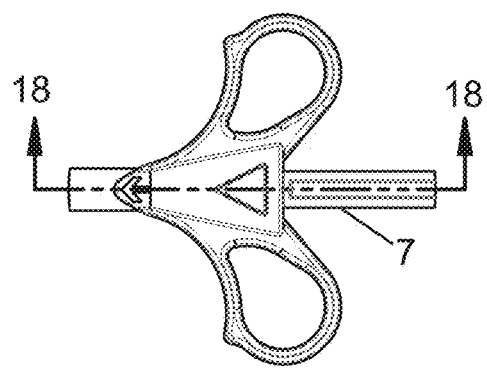
FIG. 17 is a top view of an embodiment of handle assembly of the tissue retrieval system of FIG. 1A with the actuator retracted to a position corresponding to a tissue retrieval bag in a redeployable cinched configuration.
Figure 18:
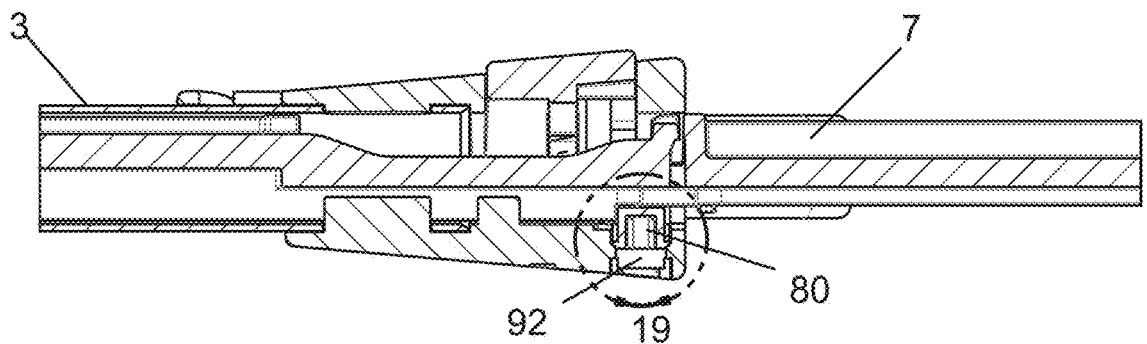
FIG. 18 is a cross sectional side view of the handle assembly of FIG. 17 with the actuator retracted to a position corresponding to a tissue retrieval bag in a redeployable cinched configuration.
Figure 19:
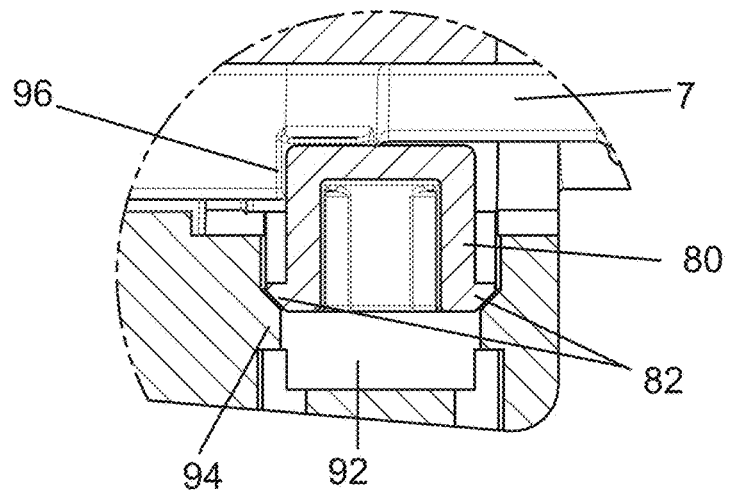
FIG. 19 is a cross sectional side view of a portion of the handle assembly of FIG. 17 detailing a blocking position of the actuator post with the actuator retracted to a position corresponding to a tissue retrieval bag in a redeployable cinched configuration.

With reference to FIGS. 14 and 15, arrangement of the bead 50, bead stop 60, and retaining latch 70 at the distal end of the introducer 3 with the actuator 7 withdrawing from the second, fully deployed position (corresponding to a tissue retrieval system positioned as illustrated in FIG. 5) are illustrated. A position of the support arms 40 and cord loop 42 with the actuator withdrawing proximally from the second deployed position is also illustrated. In the illustrated embodiment, the retaining latch 70 includes an angled contact surface at the latch tab 76 that is configured to disengage from the ledge 57 on the bead 50 during withdrawal of the actuator 7 and cinching of the retrieval bag. As the actuator 7 is retracted to cinch the retrieval bag, the bead stop 60 prevents the bead 50 from being drawn into the introducer tube. At this stage, as the retaining latch 70 is retracted relative to the bead 50, the angled contact surface on the retaining latch 70 engages with the ledge 57 on the bead 50 causing the retaining latch to deflect and ride over the ledge 57, resulting in a decoupling of the bead 50 from the retaining latch 70 (FIG. 14). The distal tip of the retaining latch 70 is positioned a sufficient distance from the distal end of the introducer tube 3 such that the retaining latch 70 can deflect, ride over the ledge 57 (FIG. 14), and then return to a non-deflected position, allowing it to be easily retracted into the introducer 3 tube (FIG. 15) for subsequent cinching of the retrieval bag. As a proximal portion of the cord loop is coupled to the actuator 7, continued withdrawal of the actuator 7 cinches the opening of the tissue retrieval bag (FIG. 6) as the bead 50 bears on the body portion of the bead stop 60. As the actuator 7 is withdrawn proximally, the support arms are withdrawn from the cuff and the bead 50 on the retrieval bag and tension is then applied to the cord loop to cinch the bag closed.

It can be desirable that in certain embodiments of tissue retrieval system in an initial, shipping and insertion configuration, the actuator is longitudinally slidable within the introducer only between the proximal position (FIG. 2) and the first deployed position (FIG. 1A). In the proximal position, the cord loop can be positioned within the introducer such that it is inaccessible. In the first deployed position, the tissue retrieval bag is coupled to the introducer. Accordingly, with the motion of the actuator limited to these positions, the potential for the tissue retrieval bag to become inadvertently decoupled from the introducer is reduced. Thus, in certain embodiments, the tissue retrieval system includes a proximal stop mechanism and a distal stop mechanism. It can be desirable that these stop mechanisms are selectively defeasible such that the actuator of a tissue retrieval system can be advanced distally beyond the first deployed position to a fully deployed position, and, once fully deployed, can be withdrawn proximally beyond the proximal position to expose the cord loop. Furthermore, it can be desirable that once the cord loop is exposed, the actuator is prevented from complete withdrawal from the introducer tube, which can create a leak path in insufflated surgical sites, and prevented from redeployment, which can undesirably advance the support arms to the surgical site. Thus, in addition to the defeasible proximal and distal stop mechanisms described above, in certain embodiments, tissue retrieval systems can comprise one or both of an actuator withdrawal stop mechanism and a redeployment lockout mechanism to limit movement of the actuator in one or both of a proximal and distal directions subsequent to cinching the tissue retrieval bag and access of the cord loop.

A proximal stop mechanism can prevent the actuator and the retrieval bag from being retracted too far into the introducer during retraction of the retrieval bag into the introducer. Prior to each insertion into the trocar during a procedure, the retrieval bag is fully retracted into the introducer by pulling the actuator in a proximal direction to the proximal position. During this retraction, the proximal stop mechanism prevents the actuator and the retrieval bag from being retracted too far into the introducer and possibly completely withdrawn from the introducer. In certain embodiments, the proximal stop mechanism also prevents the cord loop from being exposed during retraction of the retrieval bag into the introducer. In retrieval systems without features for controlling the proximal movement of the actuator, the actuator and the retrieval bag can sometimes be pulled into the handle of the device causing the retrieval bag to get jammed into the handle. Upon further proximal movement in these systems without proximal stop mechanisms, the actuator and the retrieval bag can also be pulled through the handle of the device and completely out of the introducer, causing the device to become unusable for the surgeon.

With reference to FIGS. 16-19, an embodiment of proximal stop mechanism for a tissue retrieval system is illustrated. The handle can comprise an axially moveable actuator post 80 positioned perpendicularly to the longitudinal axis of the actuator 7 that allows the retrieval bag to be retracted into the introducer 3 tube while preventing the cord loop on the actuator from being exposed. The actuator post 80 can comprise a generally cylindrical body having a first end and a second end opposite the first end. The actuator post can have one or more cantilever snap legs 82 protruding radially outwardly from the second end. The actuator post 80 is positioned in a bore 92 formed in the handle assembly. As illustrated, the bore 92 is formed in a lower handle portion 90 of the handle assembly. The cantilever snap legs 82 rest on ramps 94 within the bore 92 of the lower handle and serve to maintain the actuator post 80 in a blocking or protruding position. A lower surface of the actuator 7 is sized and dimensioned to pass freely over the actuator post 80 as the actuator is slid longitudinally between the proximal position and the first deployed position. The lower surface of the actuator 7 can further comprise a ledge 96 formed therein and positioned to engage with the actuator post 80 to prevent movement of the actuator proximally past the proximal position. In this position of the actuator, the cord loop remains contained within the handle and introducer tube (FIG. 2). Thus, when positioned in the protruding position, the actuator post 80 allows the retrieval bag to be fully retracted into the introducer tube and deployed multiple times from the introducer tube without exposing the cord loop.

In certain embodiments, the actuator post is biased to the protruding or blocking position. For example, the proximal stop mechanism can further comprise a compression spring to bias the actuator post to a protruding position to engage with the ledge on the actuator. The compression spring can be positioned within an inner diameter of the actuator post and bear against the handle assembly.

Figure 20:
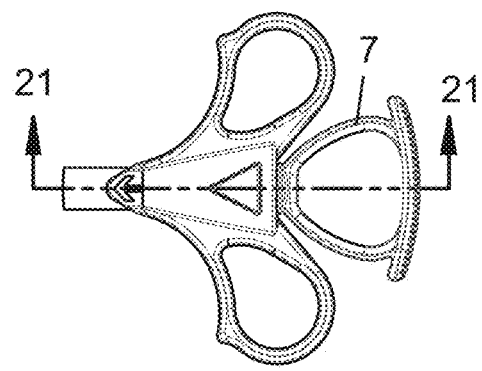
FIG. 20 is a top view of an embodiment of handle assembly of the tissue retrieval system of FIG. 1A with the actuator advanced to a position corresponding to a tissue retrieval bag in a fully deployed configuration.
Figure 21:
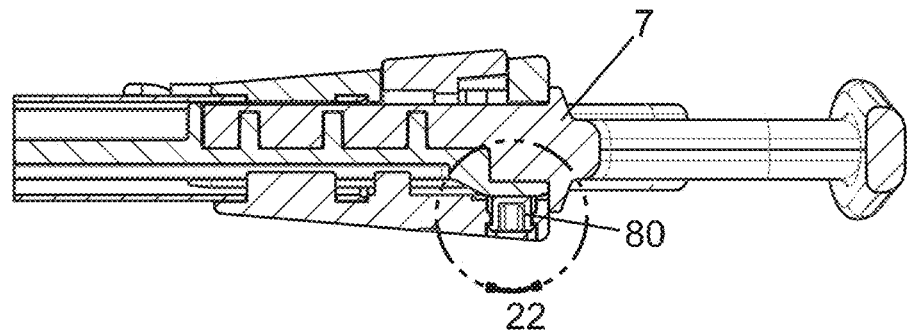
FIG. 21 is a cross sectional side view of the handle assembly of FIG. 20 with the actuator advanced to a position corresponding to a tissue retrieval bag in a fully deployed configuration.
Figure 22:
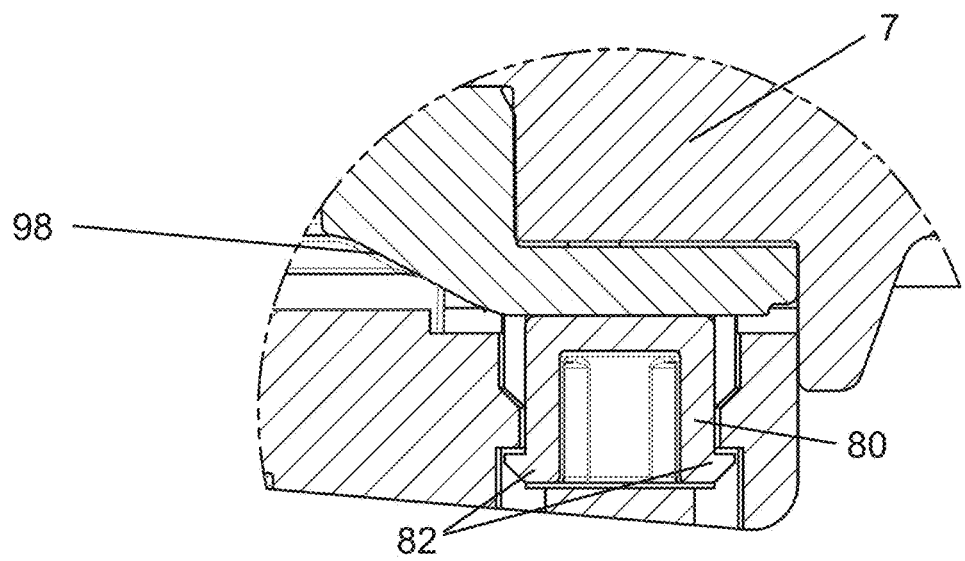
FIG. 22 is a cross sectional side view of a portion of the handle assembly of FIG. 20 detailing a recessed position of the actuator post with the actuator advanced to a position corresponding to a tissue retrieval bag in a fully deployed configuration.
Figure 23A:
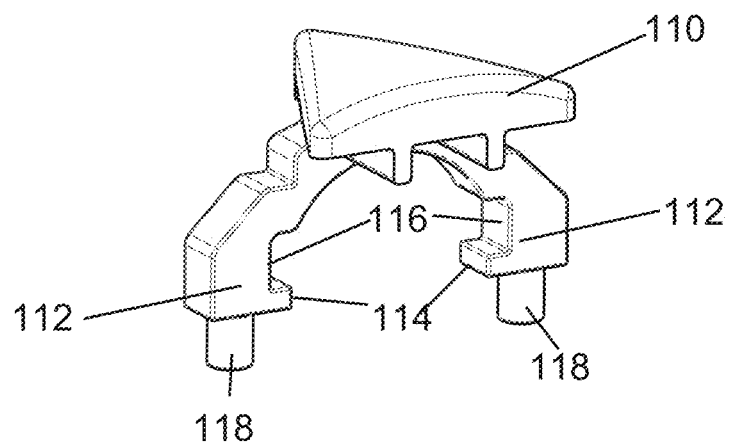
FIG. 23A is a perspective view of an embodiment of deployment release button for use with a handle assembly of the tissue retrieval system of FIG. 1A.
Figure 24A:
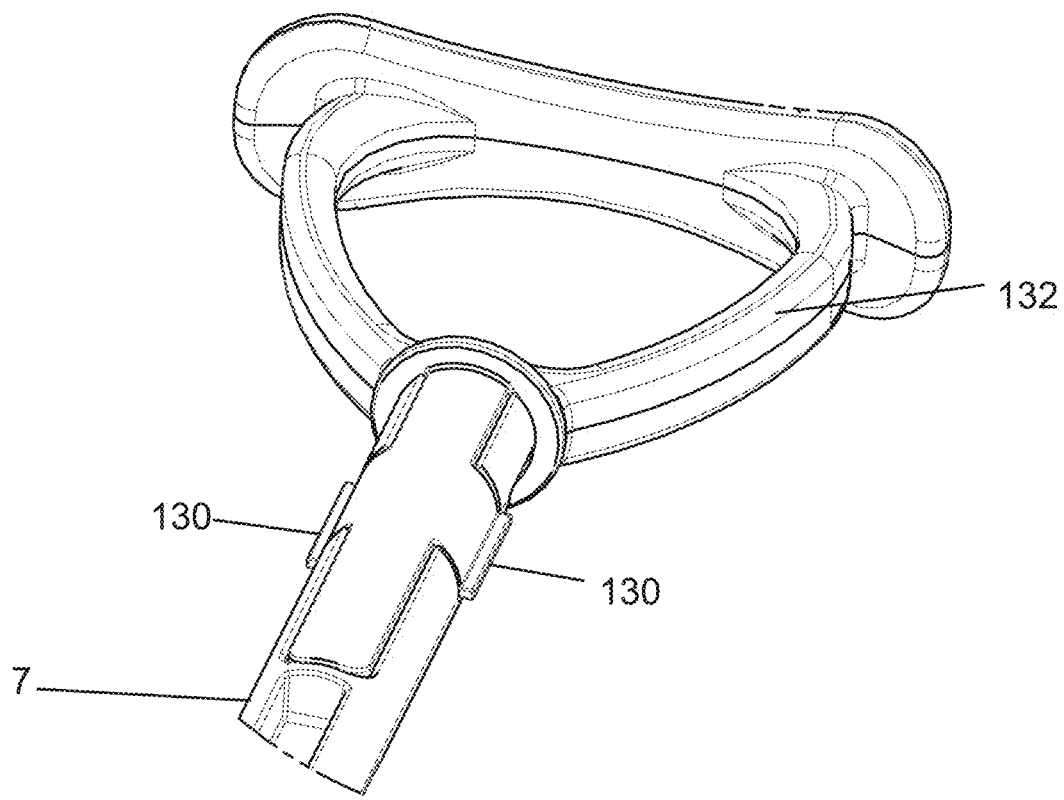
FIG. 24A is a perspective view of an embodiment of actuator handle for use with a handle assembly of the tissue retrieval system of FIG. 1A.
Figure 23B:
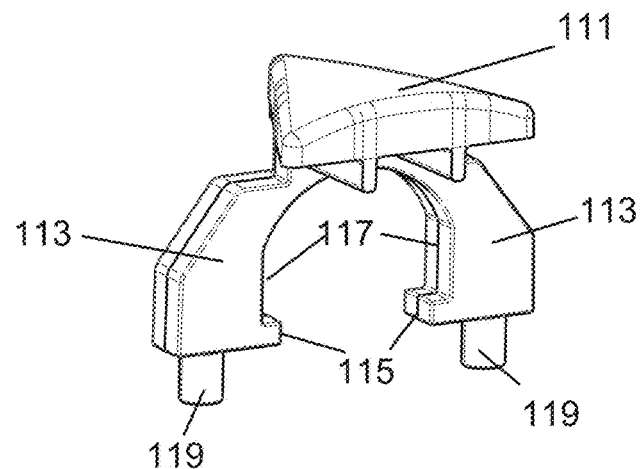
FIG. 23B is a perspective view of another embodiment of deployment release button for use with a handle assembly of the tissue retrieval system of FIG. 1A.
Figure 24B:
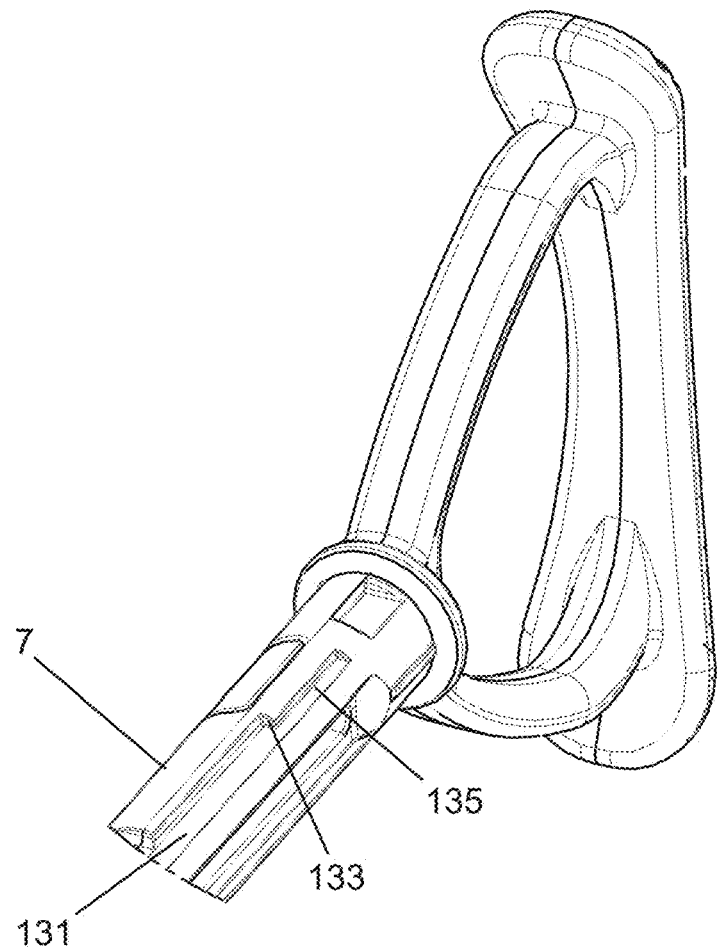
FIG. 24B is a perspective view of another embodiment of actuator handle for use with a handle assembly of the tissue retrieval system of FIG. 1A.

With reference to FIGS. 20-22, an embodiment of proximal stop mechanism is illustrated with the actuator advanced to the second, fully deployed position. In various surgical procedures it can be desirable to withdraw the actuator proximally past the proximal position after full deployment of the tissue retrieval bag and separation of the tissue retrieval bag from the actuator. With the actuator thus proximally withdrawn, the support arms can be removed from the cuff of the tissue retrieval bag and the cord loop can be accessible such that the retrieval bag can be withdrawn from a surgical site. Thus, it can be desirable that the proximal stop mechanism is defeasible upon actuation of the actuator 7 to the fully deployed position.

With continued reference to FIGS. 20-22, in certain embodiments, the actuator comprises a camming ramp 98 formed therein positioned adjacent the proximal end thereof to depress the actuator post 80 downward to a disengaged position relative to the actuator when the actuator is advanced to the fully deployed position. As the actuator 7 is advanced, the camming ramp 98 on the proximal end of the actuator contacts the actuator post 80 and cams the post downward to a non-protruding position where the cantilever snap legs 82 lock into the lower handle. With the actuator post 80 locked into a non-protruding position, the actuator 7 can be withdrawn proximally beyond the proximal position to fully tension the cord, cinch the retrieval bag, and expose the cord loop. With the cord loop exposed on the actuator 7 proximal to the handle, the surgeon can grasp and release the cord loop from the actuator, allowing the introducer and trocar to be removed from the body wall of the patient, leaving the cord loop disposed across the body wall for subsequent withdrawal of the retrieval bag from the patient.

Thus, advantageously, with a proximal stop mechanism, the cord loop of the tissue retrieval systems discussed herein are not exposed to the surgeon until the retrieval bag is cinched closed. This feature can prevent the surgeon or nurse from unintentionally grasping, cutting, releasing, or tensioning the cord loop during use of the device. In some procedures, the surgeon may need to serially contain and withdraw twenty or more tissue specimens, requiring extensive manipulation and handling of the tissue retrieval system within the patient and external to the patient by the surgeon and the nurse. The stored cord loop of the present invention obviates the chance for the cord loop to be grasped, cut, released, tensioned, or to get tangled during the extensive manipulation and handling of the device that can occur during a procedure. Without a proximal stop mechanism, other tissue retrieval systems can have a cord or line used for cinching the retrieval bag that is fully exposed to the surgeon at all times during use of the device. In certain of these devices, the cord or line is attached to the proximal end of the actuator or to the introducer handle, which can allow the surgeon or nurse to prematurely release the cord or line during the procedure resulting in the unintended release of the retrieval bag from the introducer. The cuff of the retrieval bag could also be prematurely partially cinched resulting in a reduced size of the opening of the retrieval bag and possible tearing or puncturing of the cuff of the retrieval bag by the support arms. The cord or line could also be cut or could get tangled in the device or could get tangled with other devices such as trocars during the procedure.

While defeating the proximal stop mechanism allows proximal retraction of the actuator beyond the proximal position, in certain embodiments, the handle assembly can further comprise an actuator withdrawal stop be configured to prevent complete proximal withdrawal of the actuator from the introducer tube. In certain embodiments, the handle assembly comprises a rib that mates with a slot on the actuator. The slot in the actuator has an end wall positioned to define a proximal limit of actuator travel to prevent the actuator from being fully withdrawn from the introducer during cinching of the retrieval bag for subsequent detachment of the retrieval bag from the introducer. This rib and slot combination allows the cord loop to be exposed during cinching of the retrieval bag and prevents any further retraction of the actuator. Advantageously, this actuator withdrawal stop ensures that carbon dioxide gas used to establish and maintain pneumoperitoneum within the body cavity in a surgical procedure does not leak through the introducer. In certain embodiments, a tissue retrieval system comprises an O-ring seal positioned on the actuator between the proximal end and the distal end of the actuator that maintains a seal with an inner surface of the introducer tube. Certain other retrieval systems can require that the entire actuator be withdrawn from the introducer prior to cinching of the retrieval bag. This withdrawal is typically done with the introducer inserted into a surgical site through a trocar. In these devices, as the actuator is completely withdrawn from the introducer, the retrieval bag can be hanging from the distal end of the introducer in the body cavity creating a significant leak path through the introducer for a loss of pneumoperitoneum to occur.

In certain embodiments of tissue retrieval system an O-ring that is positioned on the actuator between the proximal end and the distal end also provides an effective seal when the retrieval bag is deployed within an insufflated body cavity. The O-ring provides a seal between the actuator and the introducer tube to prevent loss of pneumoperitoneum while the surgeon is excising and placing tissue specimens in the retrieval bag. Certain other retrieval systems include seals within the handles positioned proximal to the introducer tube that attempt to seal on the actuator. These seals are not typically effective in preventing the loss of pneumoperitoneum as numerous leak paths can exist between the introducer tube and the handles, between the actuator and the introducer tube, between the upper and lower handle halves, between the handles and the introducer tube, between the seal and the actuator, and between the seal and the cord or tail of the retrieval bag.

With reference to FIGS. 23A, 24A, 25A, 26A, 27A, and 28A, an embodiment of distal stop mechanism is illustrated. In certain embodiments, a tissue retrieval system includes a distal stop mechanism to prevent movement of the actuator distally past a first deployed position in which the tissue retrieval bag remains coupled to the actuator (FIG. 1A). Desirably, such a stop allows repeated deployment of the tissue retrieval bag to sequentially retrieve multiple tissue specimens. In certain embodiments, it is desirable that the distal stop mechanism is selectively releasable or defeasible such that a surgeon can control advancement of the actuator distal of the first deployed position to a fully deployed position in which the tissue retrieval bag can be separated from the actuator.

Figure 25A:
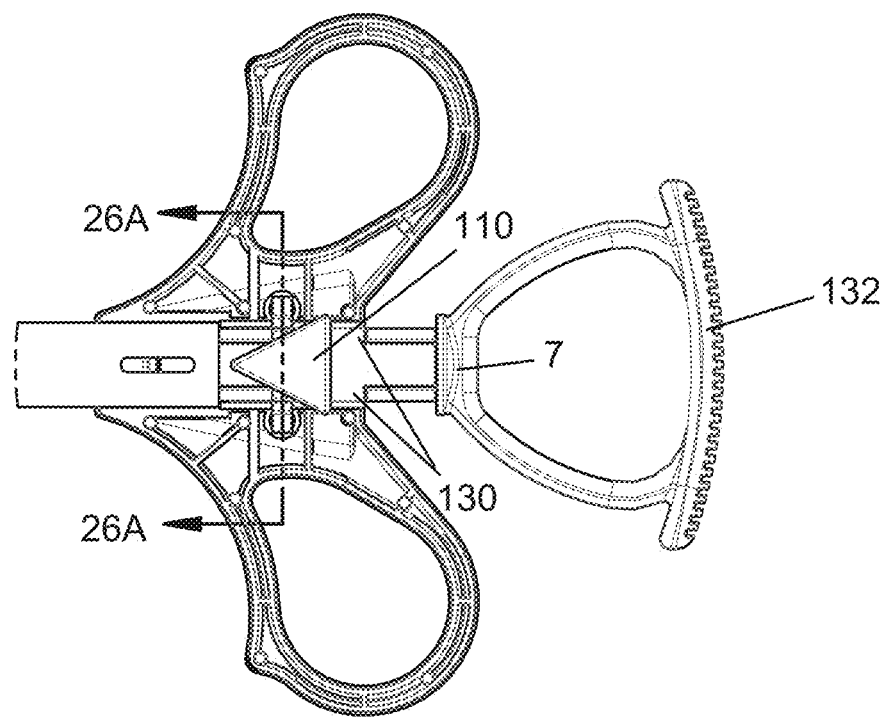
FIG. 25A is a partial cut away top view of a handle assembly of the tissue retrieval system of FIG. 1A with the actuator handle of FIG. 24A advanced to a position corresponding to a tissue retrieval bag in a first deployed configuration.
Figure 26A:
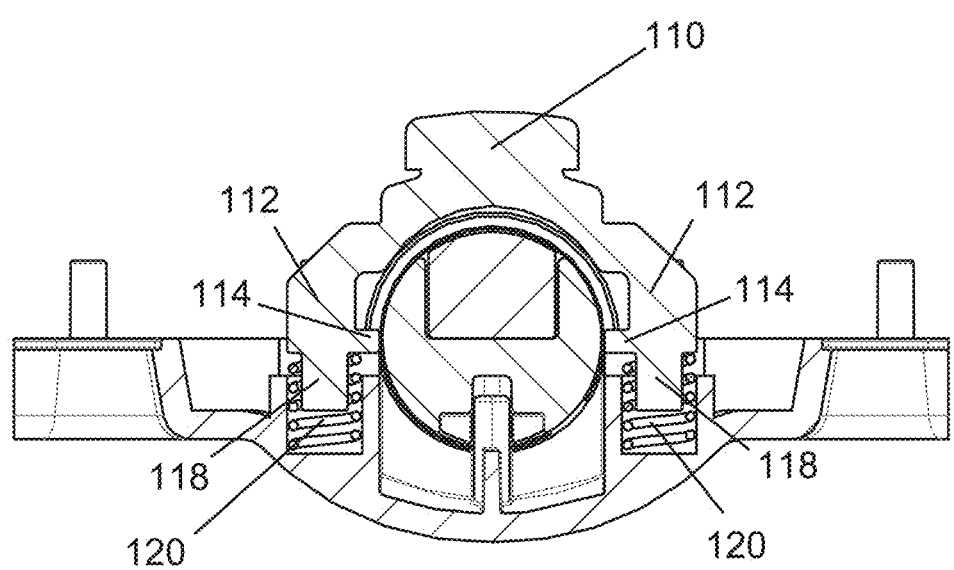
FIG. 26A is a cross-sectional end view of a handle assembly of the tissue retrieval system of FIG. 1A with the actuator handle advanced to a position corresponding to a tissue retrieval bag in a first deployed configuration and the deployment release button of FIG. 23A in a blocking position.

With reference to FIGS. 23A, 24A, 25A, and 26A, the distal stop mechanism can comprise a selectively releasable deployment latch. In certain embodiments, the deployment latch can comprise a deployment release button 110 positioned in the handle assembly. As illustrated, the deployment release button 110 is nested into the upper handle. As illustrated, the button 110 includes walls 112 that extend along each side of the actuator 7. The walls 112 include radially inwardly extending latch tabs or stop tabs 114 and recesses 116 positioned radially outwardly of the stop tabs 114. The deployment release button 110 includes two posts 118 extending from a lower surface of the walls 112. Each of the posts 118 can be positioned in a corresponding bore in the handle assembly and can retain a compression spring 120 such that the posts 118 and compression springs 120 are nested into the lower handle. The compression springs 120 bias the button 110 upward when the handle assembly is oriented as illustrated in FIG. 26A. In the illustrated embodiment, the button 110 has a generally triangular shape aligned to convey to a user a direction of travel of the actuator 7. In other embodiments, the deployment release button can have a square, circular, oval, or other shape. In certain embodiments an icon or stylized logo can be added to the button to convey information to a user.

With continued reference to FIGS. 23A, 24A, 25A, and 26A, the actuator 7 can comprise radially protruding ribs 130 adjacent the proximal end thereof. In certain embodiments, the actuator can comprise a separately molded thumb loop 132, which can be pressed onto the actuator 7 via interference pins and holes. The thumb loop 132 can include the ribs 130 molded along its longitudinal axis.

With reference to FIGS. 25A and 26A, the handle assembly of a tissue retrieval system is illustrated with the actuator in a first deployed position and a distal stop mechanism engaged such that the deployment latch is in a latched configuration. The deployment release button 110 is biased upward such that the stop tabs 114 of the walls 112 interfere with and block distal movement of the ribs 130 of the actuator 7. As the actuator 7 is initially advanced to deploy the retrieval bag, the ribs on the thumb loop contact the walls on the button and prevent the actuator from being advanced beyond its initial position. Thus, when the deployment release button 110 is not pressed, the button 110 allows the actuator 7 to only be advanced to the first deployed position, with the retrieval bag deployed from a distal end of the introducer but coupled to the actuator and where the retrieval bag can be subsequently retracted into the introducer (FIG. 1A).

Figure 27A:
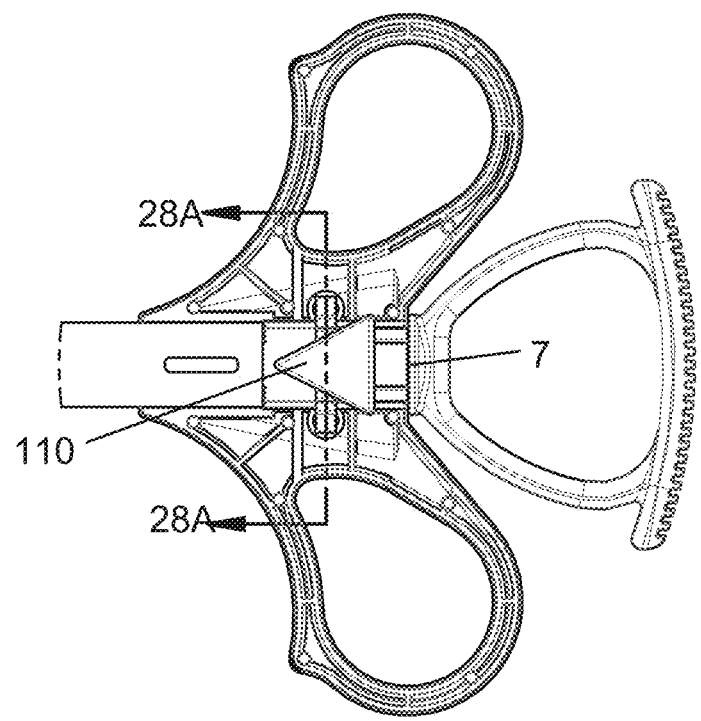
FIG. 27A is a partial cut away top view of a handle assembly of the tissue retrieval system of FIG. 1A with the actuator handle of FIG. 24A advanced to a position corresponding to a tissue retrieval bag in a fully deployed configuration.
Figure 28A:
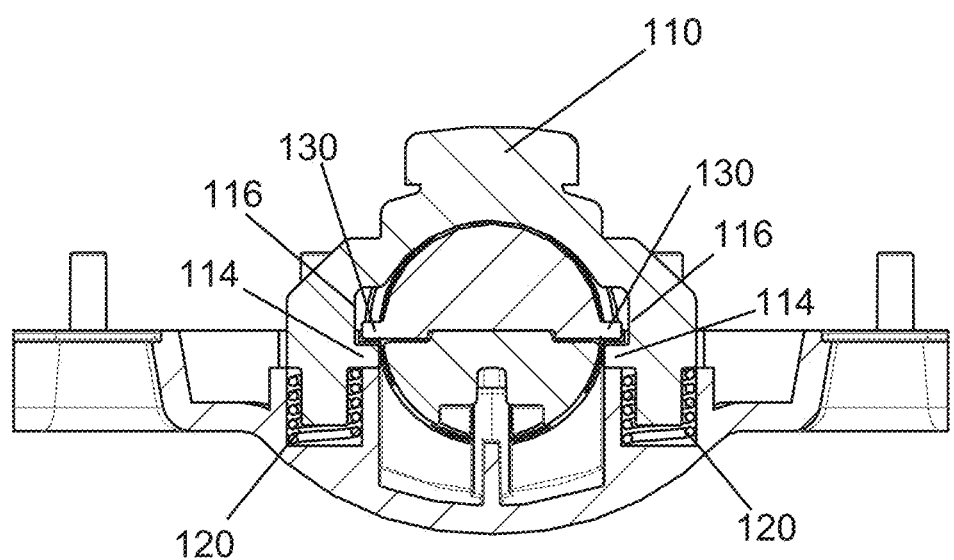
FIG. 28A is a cross-sectional end view of a handle assembly of the tissue retrieval system of FIG. 1A with the actuator handle of FIG. 24A advanced to a position corresponding to a tissue retrieval bag in a fully deployed configuration and the deployment release button of FIG. 23A in a depressed position.

With reference to FIGS. 27A and 28A, the handle assembly of a tissue retrieval system is illustrated with the actuator in a second, fully deployed position and a distal stop mechanism released. When it is desired to release the tissue retrieval bag from the actuator during a procedure, a surgeon can depress the deployment release button 110 on the handle assembly. When the button 110 is pressed downward, the walls 112 on the button move to position the stop tabs 114 out of alignment with the ribs 130 on the actuator 7 allowing the actuator to then be advanced to its fully deployed position. As the actuator 7 is advanced, the ribs 130 can slide within the recesses 116 of the walls 112. The compression springs 120 bias the button 110 upward and serve to return the button to a raised position (FIGS. 25A, 26A) after the button 110 has been pressed and then released. Thus, when the button 110 is pressed downward to defeat the distal stop mechanism, the actuator can then be advanced to its fully deployed position, where the retrieval bag can subsequently be cinched closed and detached from the introducer. In certain embodiments, advancing the actuator to the fully deployed position also defeats a proximal stop mechanism such as the actuator post described and illustrated with reference to FIGS. 16-22. The actuator can then be fully retracted to tension the cord loop, cinch the retrieval bag, and expose the small loop of cord on the actuator.

Figure 25B:
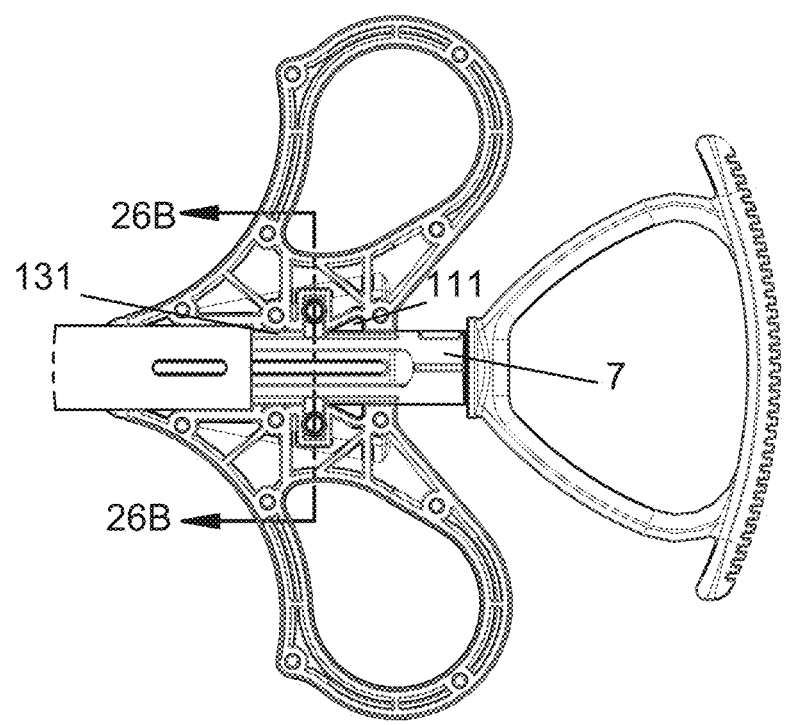
FIG. 25B is a partial cut away bottom view of a handle assembly of the tissue retrieval system of FIG. 1A with the actuator handle of FIG. 24B advanced to a position corresponding to a tissue retrieval bag in a first deployed configuration.
Figure 26B:
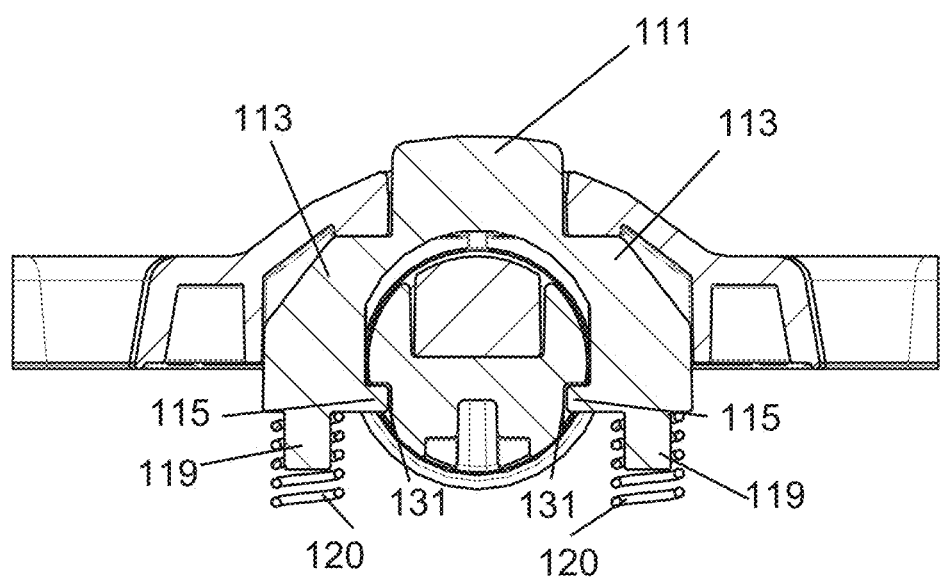
FIG. 26B is a cross-sectional end view of a handle assembly of the tissue retrieval system of FIG. 1A with the actuator handle advanced to a position corresponding to a tissue retrieval bag in a first deployed configuration and the deployment release button of FIG. 23B in a blocking position.

With reference to FIGS. 23B, 24B, 25B, 26B, 27B, and 28B, another embodiment of distal stop mechanism is illustrated. Similar to the embodiment discussed above with reference to FIGS. 23A, 24A, 25A, and 26A, the distal stop mechanism can comprise a selectively releasable deployment latch. In certain embodiments, the deployment latch can comprise a deployment release button 111 positioned in the handle assembly. As illustrated, the deployment release button 111 is nested into the upper handle. As illustrated, the button 111 includes walls 113 that extend along each side of the actuator 7. The walls 113 include radially inwardly extending latch tabs or stop tabs 115 and recesses 117 positioned radially outwardly of the stop tabs 115. The deployment release button 111 includes two posts 119 extending from a lower surface of the walls 113. Each of the posts 119 can be positioned in a corresponding bore in the handle assembly and can retain a compression spring 120 such that the posts 119 and compression springs 120 are nested into the lower handle. The compression springs 120 bias the button 111 upward when the handle assembly is oriented as illustrated in FIG. 26B. In the illustrated embodiment, the button 111 has a generally triangular shape aligned to convey to a user a direction of travel of the actuator 7. In other embodiments, the deployment release button can have a square, circular, oval, or other shape. In certain embodiments an icon or stylized logo can be added to the button to convey information to a user.

With continued reference to FIGS. 23B, 24B, 25B, and 26B, the actuator 7 can comprise at least one longitudinally extending rail, slot, or groove 131 positioned such that the stop tabs 115 of the button 111 are in sliding engagement with an upper edge of the groove 131. The button 111 is biased such that the stop tabs 115 are adjacent the upper edge of the groove 131. In certain embodiments, the button can be sized and configured such that the stop tabs 115 are adjacent but out of contact with the upper edge of the groove 131 to prevent frictional contact therebetween as the actuator 7 is slid. As illustrated, the groove 131 comprises a proximal end wall 133 adjacent the proximal end thereof. The groove 131 further comprises a deployment segment 135 proximal the proximal end wall 133. The deployment segment can extend along an axis parallel to a longitudinal axis of the portion of the groove 131 distal of the proximal end wall 133 and offset therefrom by a height of the proximal end wall 133.

With reference to FIGS. 25B and 26B, the handle assembly of a tissue retrieval system is illustrated with the actuator in a first deployed position and a distal stop mechanism engaged such that the deployment latch is in a latched configuration. The deployment release button 111 is biased upward such that the stop tabs 115 of the walls 113 interfere with the proximal end wall 133 of the groove 131 and block further distal movement of the actuator 7. Thus, when the deployment release button 111 is not pressed, the button 111 allows the actuator 7 to only be advanced to the first deployed position, with the retrieval bag deployed from a distal end of the introducer but coupled to the actuator and where the retrieval bag can be subsequently retracted into the introducer (FIG. 1A).

Figure 27B:
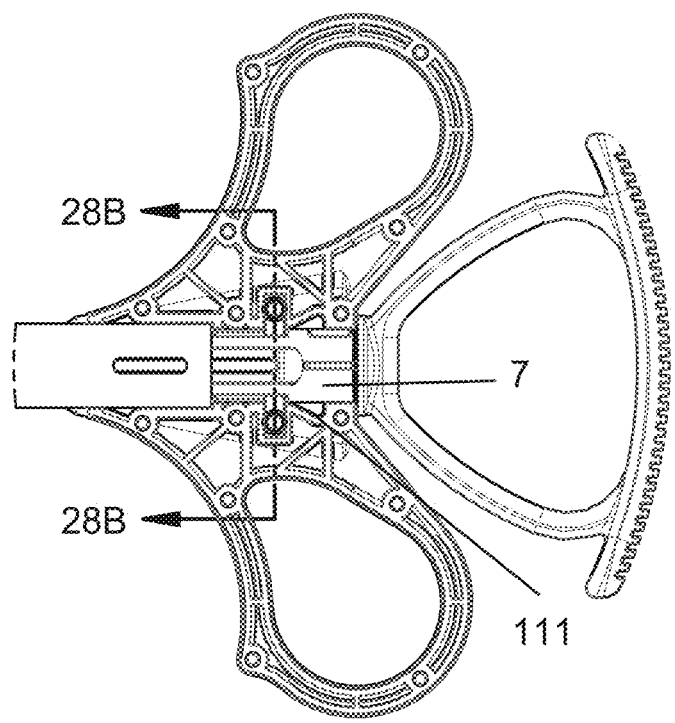
FIG. 27B is a partial cut away bottom view of a handle assembly of the tissue retrieval system of FIG. 1A with the actuator handle of FIG. 24B advanced to a position corresponding to a tissue retrieval bag in a fully deployed configuration.
Figure 28B:
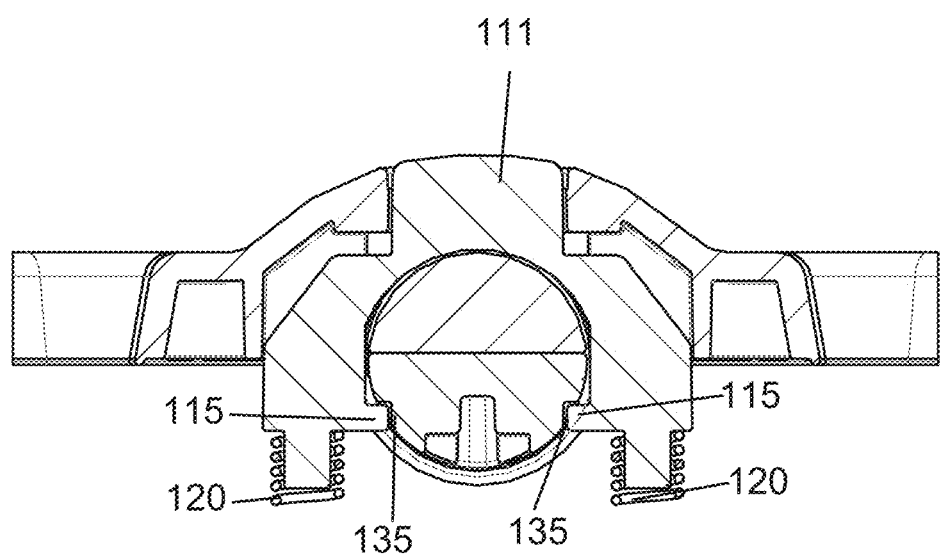
FIG. 28B is a cross-sectional end view of a handle assembly of the tissue retrieval system of FIG. 1A with the actuator handle of FIG. 24B advanced to a position corresponding to a tissue retrieval bag in a fully deployed configuration and the deployment release button of FIG. 23B in a depressed position.

With reference to FIGS. 27B and 28B, the handle assembly of a tissue retrieval system is illustrated with the actuator in a second, fully deployed position and a distal stop mechanism released. When it is desired to release the tissue retrieval bag from the actuator during a procedure, a surgeon can depress the deployment release button 111 on the handle assembly. When the button 111 is pressed downward, the walls 113 on the button move to position the stop tabs 115 out of alignment with the proximal end wall 133 of the groove 131 on the actuator 7 and into alignment with the deployment segment 135 of the groove, allowing the actuator to then be advanced to its fully deployed position. As the actuator 7 is advanced, the stop tabs 115 can slide within the deployment segment 135 of the groove 131. The compression springs 120 bias the button 111 upward and serve to return the button to a raised position (FIGS. 25B, 26B) after the button 111 has been pressed and then released. Thus, when the button 111 is pressed downward to defeat the distal stop mechanism, the actuator can then be advanced to its fully deployed position, where the retrieval bag can subsequently be cinched closed and detached from the introducer. In certain embodiments, advancing the actuator to the fully deployed position also defeats a proximal stop mechanism such as the actuator post described and illustrated with reference to FIGS. 16-22. The actuator can then be fully retracted to tension the cord loop, cinch the retrieval bag, and expose the small loop of cord on the actuator.

Figure 27C:
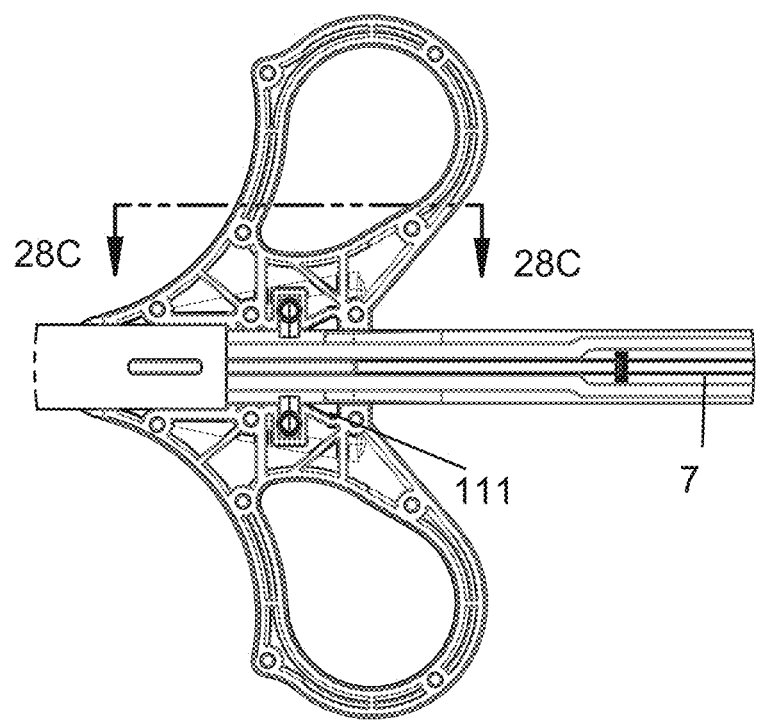
FIG. 27C is a partial cut away bottom view of a handle assembly of the tissue retrieval system of FIG. 1A with the actuator handle of FIG. 24B retracted to a position corresponding to a tissue retrieval bag in a fully cinched configuration.
Figure 28C:
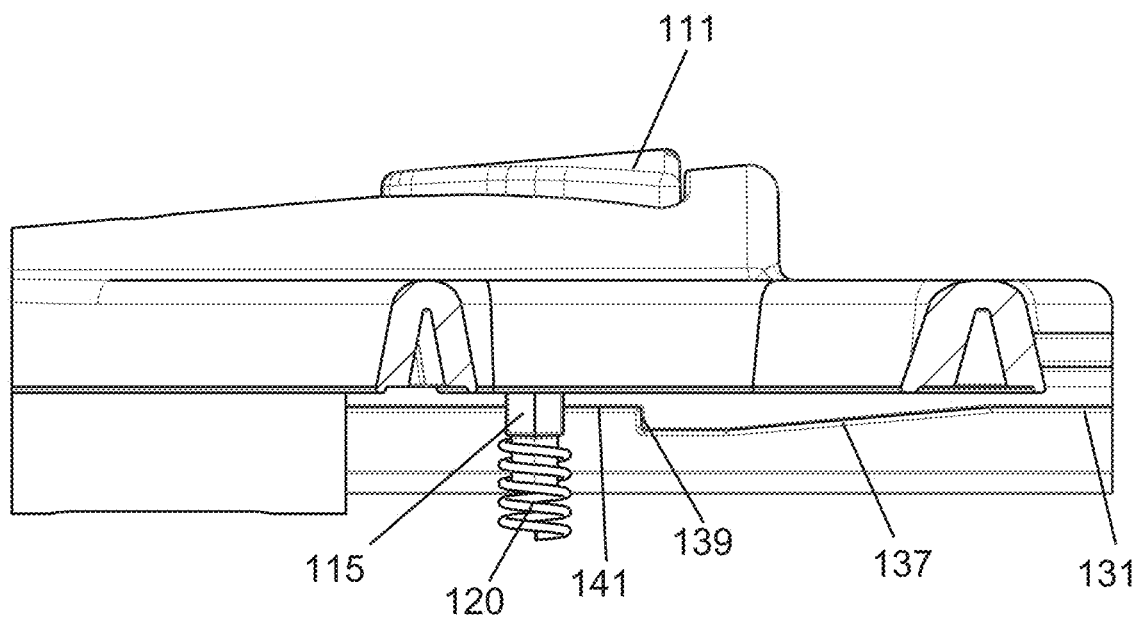
FIG. 28C is a cross-sectional side view of a handle assembly of the tissue retrieval system of FIG. 1A with the actuator handle of FIG. 24B retracted to a position corresponding to a tissue retrieval bag in a fully cinched configuration.

With reference to FIGS. 27C and 28C, the handle assembly of a tissue retrieval system is illustrated with the actuator proximally retracted to a position corresponding to a cinched tissue retrieval bag (FIG. 6A) following full deployment of the tissue retrieval bag. In some embodiments, the distal stop mechanism of FIGS. 23B, 24B, 25B, 26B, 27B, and 28B further comprises a redeployment latch mechanism. As illustrated, the groove 131 of the actuator extends longitudinally distally along the actuator 7 to a position corresponding to a proximally retracted position of the actuator 7 with the tissue retrieval bag in a cinched configuration (FIG. 6A). The groove 131 comprises a redeployment latch ramp 137, a redeployment latch end wall 139, and a redeployment latch segment 141 formed in an upper edge of the groove and positioned longitudinally on the actuator 7 adjacent this proximally retracted position. Thus, as the actuator is proximally retracted relative to the handle assembly to cinch the tissue retrieval bag, the stop tabs 115 of the button 111 are biased into engagement with the redeployment latch ramp 137, over the redeployment latch end wall 139, and adjacent to an upper edge of the redeployment latch segment 141, as illustrated in FIG. 28C. An attempt to distally advance the actuator 7 from this proximally retracted position would cause the stop tabs 115 to engage the redeployment latch end wall 139, restricting further distal movement of the actuator 7. Thus, the redeployment latch mechanism can desirably prevent unintended redeployment of the support arms once the tissue retrieval system has been operated to fully cinch the tissue retrieval bag.

Figure 29:
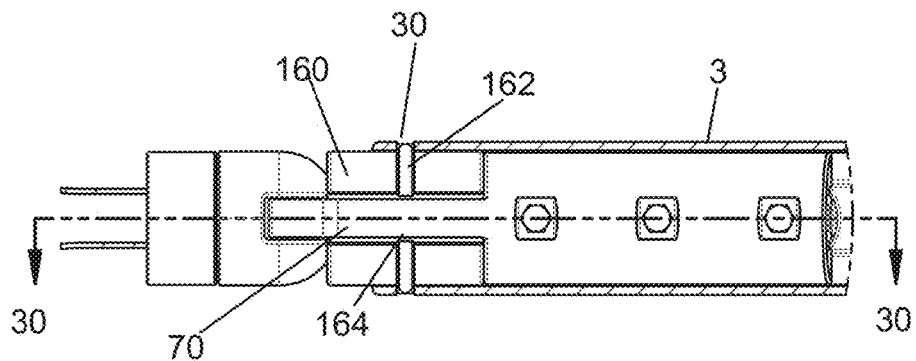
FIG. 29 is a partial cut away bottom view of an embodiment of retention latch, bead stop, and guide bead for use in a tissue retrieval system with the actuator position advanced to correspond to the tissue retrieval bag in a fully deployed configuration.
Figure 30:
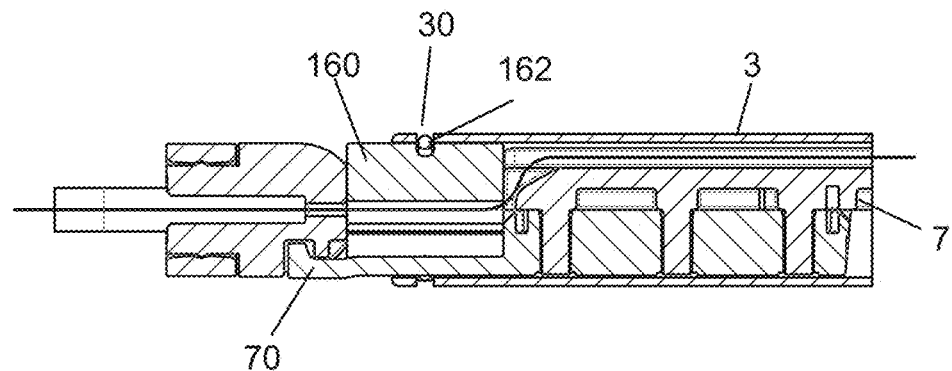
FIG. 30 is a cross-sectional side view of the embodiment of retention latch, bead stop, and guide bead of FIG. 29.

With reference to FIGS. 29-30, in certain embodiments a tissue retrieval system can include a bead stop 160 having a snap ring 162 such as a stainless steel snap ring rather than a bead stop 60 as described an illustrated with respect to FIG. 9. Other aspects of the tissue retrieval systems described above can be used in combination with the bead stop 160. A slot 30 in the introducer tube can be sized and configured to receive snap ring 162 to lockingly engage the bead stop 160. The snap ring would remain in a compressed state within the introducer tube with the actuator in its first deployed position for redeployable use of the retrieval bag. When the actuator 7 is advanced to its fully deployed position (FIGS. 29-30) to enable cinching of the retrieval bag, the snap ring expands into the slot 162 on the introducer tube and prevents the bead 50 and retrieval bag from being retracted into the introducer tube. The snap ring 162 can comprise a gap 164 formed therein and aligned with a corresponding gap in the bead stop 160, and the retaining latch 70 can extend through the gap 164.

Figure 31A:
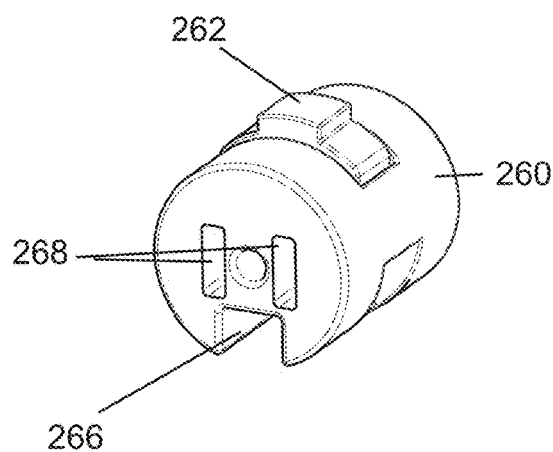
FIG. 31A is a perspective view of an embodiment of bead stop for use in a tissue retrieval system.
Figure 32A:
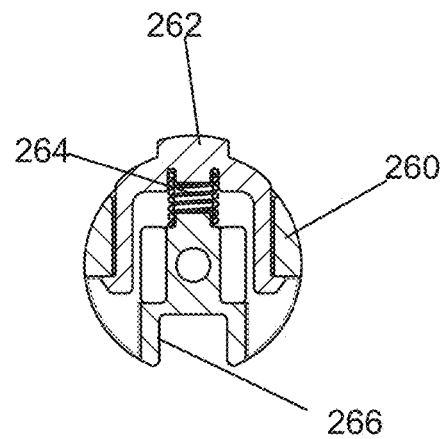
FIG. 32A is a cross-sectional view of the bead stop of FIG. 31A.

With reference to FIGS. 31A and 32A, in certain embodiments a tissue retrieval system can include a bead stop 260 having a spring-biased clip 262 rather than a bead stop 60 as described an illustrated with respect to FIG. 9. Other aspects of the tissue retrieval systems described above can be used in combination with the bead stop 260. The introducer tube can include an aperture sized and configured to receive the clip 262 to lockingly engage the bead stop when the actuator is moved to a fully deployed position. The bead stop 260 can further comprise a compression spring 264 positioned between the clip 262 and the bead stop body. The clip 262 remains in a compressed state with the actuator between the proximal position and the first deployed position for redeployable use of the retrieval bag. When the actuator is advanced to its fully deployed position to enable cinching of the retrieval bag, the clip 262 is driven upward by the compression spring 264 to engage with the aperture in the introducer tube to prevent the bead and retrieval bag from being retracted into the introducer tube. The bead stop 260 can comprise a channel 266 through which a retaining latch of a tissue retrieval system can extend. The bead stop 260 can further comprise a pair of axially spaced slots 268 and a passage sized and configured to receive support arms and the cord loop of the tissue retrieval system therethrough.

Figure 31B:
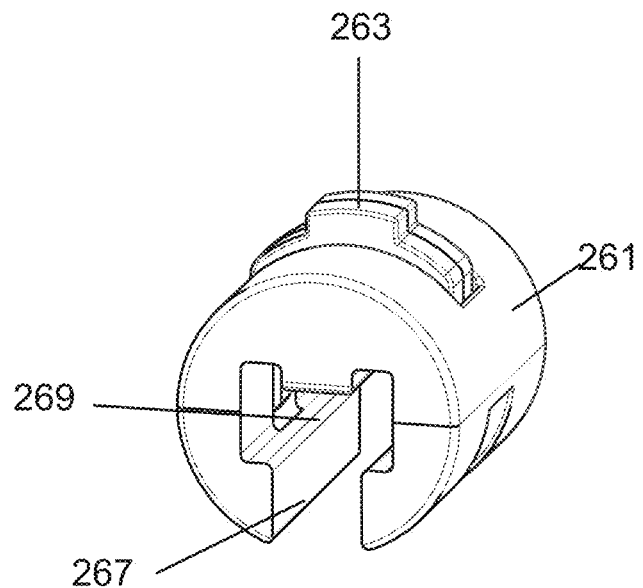
FIG. 31B is a perspective view of an embodiment of bead stop for use in a tissue retrieval system.
Figure 32B:
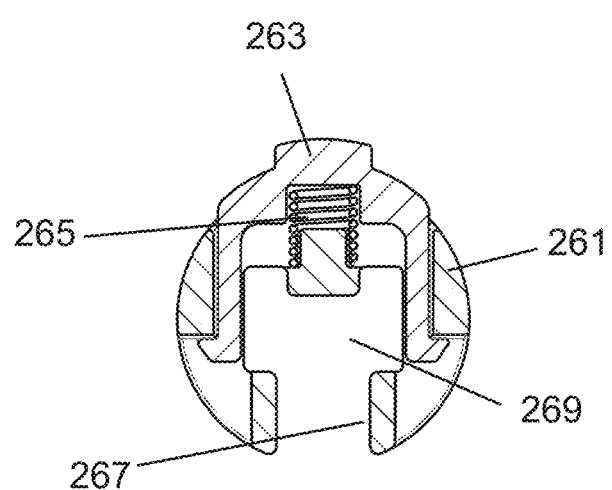
FIG. 32B is a cross-sectional view of the bead stop of FIG. 31B.

With reference to FIGS. 31B and 32B, in certain embodiments a tissue retrieval system can include another embodiment of bead stop 261 having a spring-biased clip 263 similar to the bead stop 260 of FIGS. 31A and 32A. The bead stop 261 can further comprise a compression spring 265 positioned between the clip 263 and the bead stop body. The bead stop 261 can comprise a channel 267 through which a retaining latch of a tissue retrieval system can extend. Unlike the bead stop 260 of FIGS. 31A and 32A, the channel 267 of the bead stop 261 can be contiguously formed with a central recess 269 sized and configured to receive support arms and the cord loop of the tissue retrieval system therethrough. Desirably, this central recess 269 contiguously formed with the channel 267 enhances ease and speed of assembly of the bead stop 261 with the support arms and cord loop during assembly of the tissue retrieval system.

Figure 33:
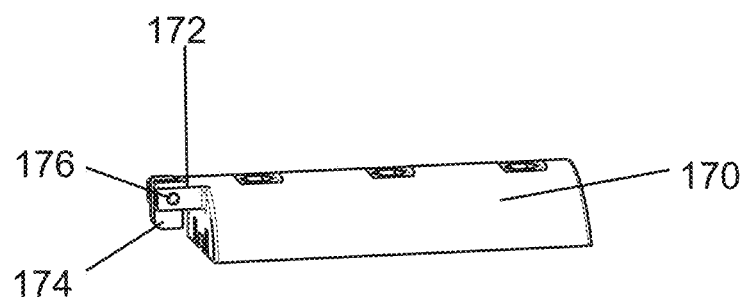
FIG. 33 is a perspective view of an embodiment of retention latch for use in a tissue retrieval system.
Figure 34:
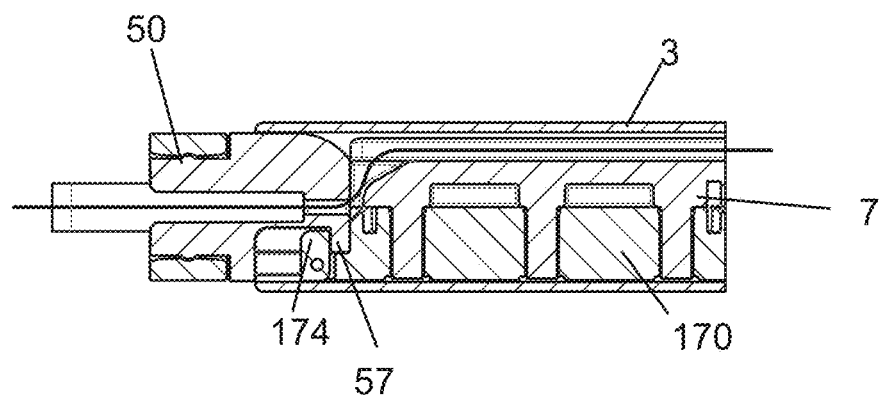
FIG. 34 is a cross-sectional side view of the retention latch of FIG. 33 engaged with a guide bead of a tissue retrieval system with the actuator advanced to a first deployed position.
Figure 35:
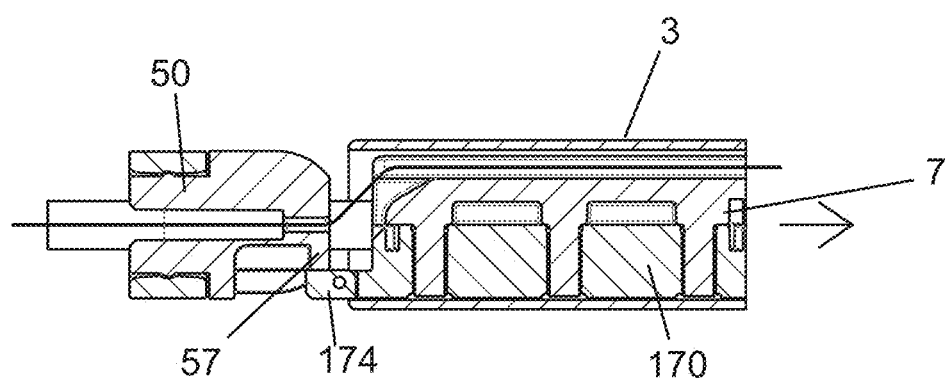
FIG. 35 is a cross-sectional side view of the retention latch of FIG. 33 engaged with a guide bead of a tissue retrieval system with the actuator advanced to a fully deployed position.

With reference to FIGS. 33-35, in certain embodiments, a redeployable tissue retrieval system can comprise an actuator cap having a rotatable retaining latch. As illustrated, the actuator cap 170 includes a forked distal extension 172 with a rotating latch 174 positioned on a pin 176 within the fork on the extension. The rotating latch 174 can rotate about the pin 176 and releasably couples with the ledge 57 on the bead 50 to retain the bead 50 and the retrieval bag to the actuator 7. With the actuator 7 slidable between the proximal position and first deployed position (FIG. 34) for redeployable use of the retrieval bag, the rotating latch 174 is engaged with the ledge 57 on the bead 50 and is constrained from rotating by the introducer 3 tube. When the actuator is advanced to its fully deployed position (FIG. 35) to enable cinching of the retrieval bag, the rotating latch 174 is positioned outside of the introducer 3 tube and is free to rotate. As the actuator 7 is retracted to cinch the retrieval bag, the rotating latch 174 rotates to a position to where it decouples from the bead 50. In certain embodiments of tissue retrieval system, the actuator cap 170 having a rotating latch 174 can be used without a bead stop (FIGS. 34-35). With no bead stop, the retrieval bag material near the bead 50 can bunch up outside of the introducer 3 tube to enable cinching. In other embodiments, the actuator cap 170 having a rotating latch 174 can be used in combination with a bead stop. In these embodiments, the forked extension on the actuator cap 170 extends through a channel in the bead stop.

Figure 36:
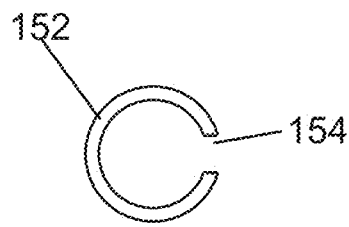
FIG. 36 is an end view of a snap ring for use with certain embodiments of guide bead in a tissue retrieval system.
Figure 37:
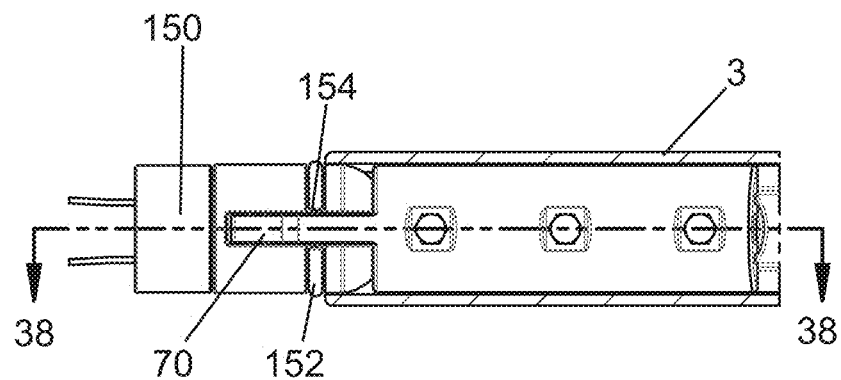
FIG. 37 is partial cut away bottom view of an embodiment of tissue retrieval system having the snap ring of FIG. 36 with the actuator advanced to a fully deployed position.
Figure 38:
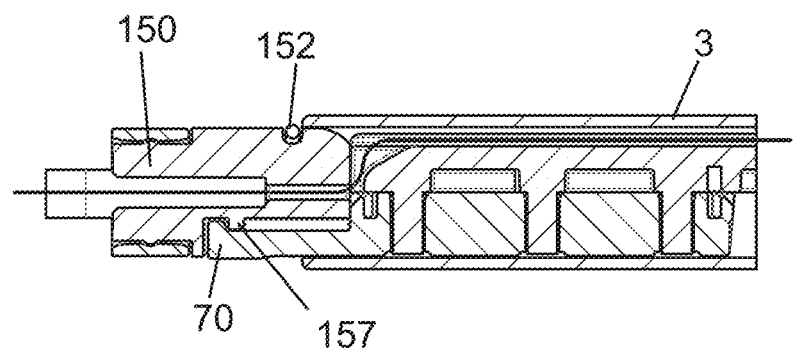
FIG. 38 is a cross-sectional side view of the tissue retrieval system of FIG. 37.
Figure 39:
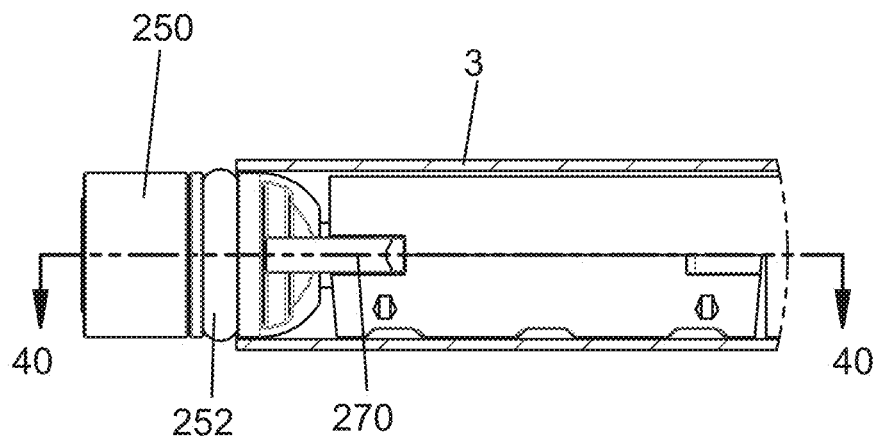
FIG. 39 is partial cut away side view of a distal end of an embodiment of tissue retrieval system having retaining latches with an actuator positioned in a fully deployed position.
Figure 40:
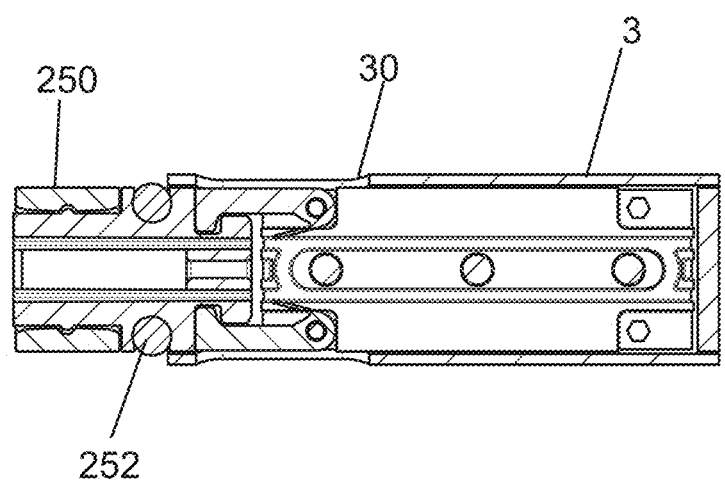
FIG. 40 is a cross-sectional top view of the tissue retrieval system of FIG. 39.
Figure 41:
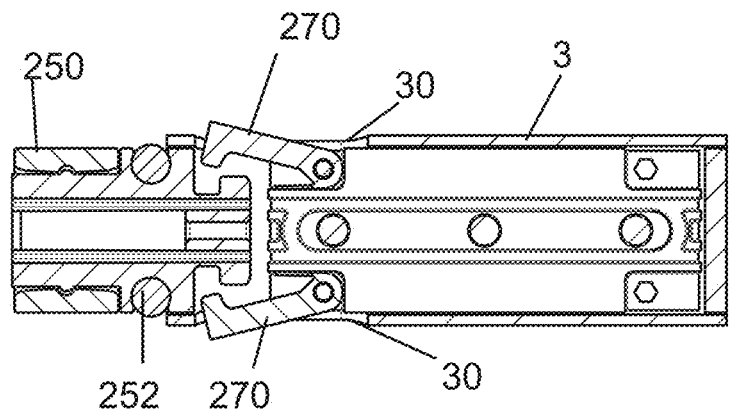
FIG. 41 is a cross sectional top view of the tissue retrieval system of FIG. 39 with actuator partially withdrawn and the retaining latches decoupling from the guide bead.

With reference to FIGS. 36-38, in certain embodiments, a tissue retrieval system can comprise a bead 150 having a radially expandable element such as a snap ring 152 positioned thereon. The snap ring 152 can be positioned around a proximal portion of the bead 150. The proximal portion of the bead 150 with the snap ring 152 remains within the introducer 3 tube with the actuator slidable between the proximal position and the first deployed position for redeployable use of the retrieval bag. During redeployable use of the retrieval bag, the snap ring 152 would remain in a compressed state within the introducer 3 tube and have a first outer diameter defined by an inner diameter of the introducer 3 tube. When the actuator is advanced to its fully deployed position (FIGS. 37-38), the snap ring 152 would be positioned outside of the introducer tube where it would expand to a second outer diameter larger than the inner diameter of the introducer tube and would prevent the bead and the retrieval bag from being retracted into the introducer 3 tube, enabling the cinching of the retrieval bag. Thus, in these embodiments tissue retrieval systems can prevent reentry of the bead into the introducer without a bead stop. The snap ring 152 comprises a gap 154 to accommodate the retaining latch 70. In the illustrated embodiment, the retaining latch 70 extends through the gap 154 in the snap ring 152 such that the distal tip of the retaining latch 70 would be positioned distal to the snap ring 152. With the actuator advanced distally to the second deployed position, as the snap ring 152 contacts the distal end of the introducer tube, the distal tip of the retaining latch 70 would be positioned outside of the introducer tube and would decouple from the ledge 157 on the bead 150 as the actuator is retracted.

In other embodiments including a guide bead 150 with snap ring 152, the distal tip of the retaining latch 70 is positioned proximal to the snap ring such that the retaining latch remains positioned within the introducer tube with the actuator in the fully deployed position. When the actuator is advanced to its fully deployed position, the snap ring would expand to prevent the bead and the retrieval bag from being retracted into the introducer tube. The distal tip of the retaining latch would mate with a slot in the introducer tube sufficiently sized to allow the retaining latch to deflect and decouple from the ledge on the bead and enable cinching of the retrieval bag.

With reference to FIGS. 39-42, in certain embodiments, a tissue retrieval system can comprise a bead 250 including an O-ring 252 that would serve to prevent the bead 250 and the retrieval bag from being retracted into the introducer tube to enable cinching of the retrieval bag. Thus, in these embodiments tissue retrieval systems can prevent reentry of the bead into the introducer without a bead stop. In the illustrated embodiment, the O-ring 252 is positioned around a proximal portion of the bead 250. The proximal portion of the bead with the O-ring remains within the introducer 3 tube with the actuator in its initial position slidably movable between the proximal position and first deployed position for redeployable use of the retrieval bag. During redeployable use of the retrieval bag, the O-ring 252 would remain in a compressed state within the introducer tube. When the actuator is advanced distally to its fully deployed position (FIGS. 39-40), the O-ring 252 would be positioned outside of the introducer tube where it would expand to a larger diameter and would prevent the bead 250 and the retrieval bag from being retracted into the introducer tube, enabling cinching of the retrieval bag.

Figure 42:
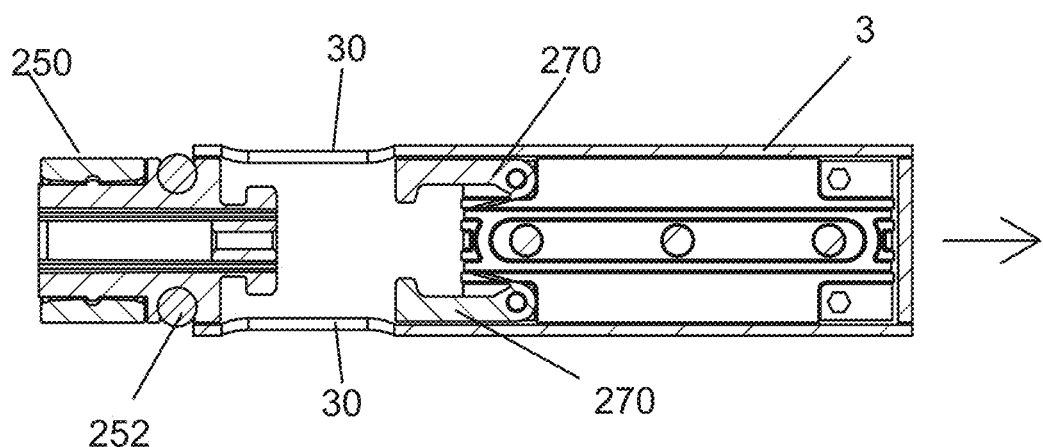
FIG. 42 is a cross sectional top view of the tissue retrieval system of FIG. 39 with actuator withdrawn and the retaining latches decoupled from the guide bead.

With continued reference to FIGS. 39-42, in certain embodiments of tissue retrieval system, a guide bead 250 having an O-ring 252 is be used in conjunction with one or two retaining latches 270. In the illustrated embodiment, the retaining latches 270 releasably engage the bead 250 proximal to the O-ring 252 and remain positioned within the introducer tube with the actuator advanced to a fully deployed position. The introducer 3 tube can comprise corresponding slots 30 sized and positioned to allow the retaining latches to deflect radially outwardly (FIG. 41) to decouple from the ledges on the bead and enable cinching of the retrieval bag (FIG. 42). In various embodiments, the retaining latches comprise separate components mechanically trapped, pivotably coupled, or otherwise attached to the actuator cap. In certain embodiments, the retaining latches are biased radially outwardly. For example, in certain embodiments, the retaining latches include integral leaf springs to bias the latches to a radially expanded position.

With reference to FIGS. 43-55, in certain embodiments, it is desirable that the bead is securely coupled to the retrieval bag to remain coupled for multiple deployment and cinch cycles of the retrieval bag in a surgical procedure. In still other embodiments, certain aspects of the beads of FIGS. 43-55 can be combined with other aspects described with respect to the beads of FIGS. 36-42.

Figure 43:
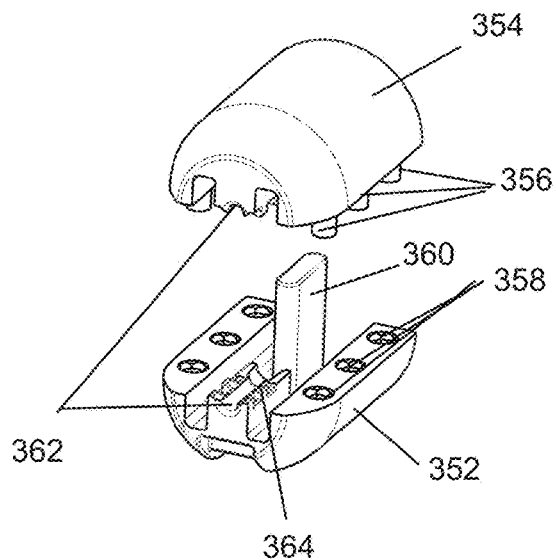
FIG. 43 is an exploded perspective view of an embodiment of guide bead for a tissue retrieval system.
Figure 44:
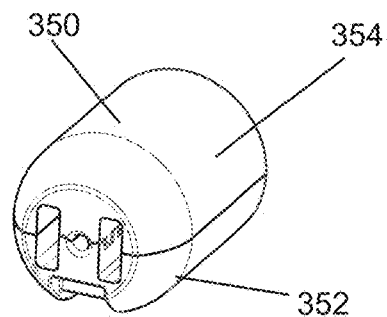
FIG. 44 is a perspective view of the guide bead of FIG. 43.
Figure 45:
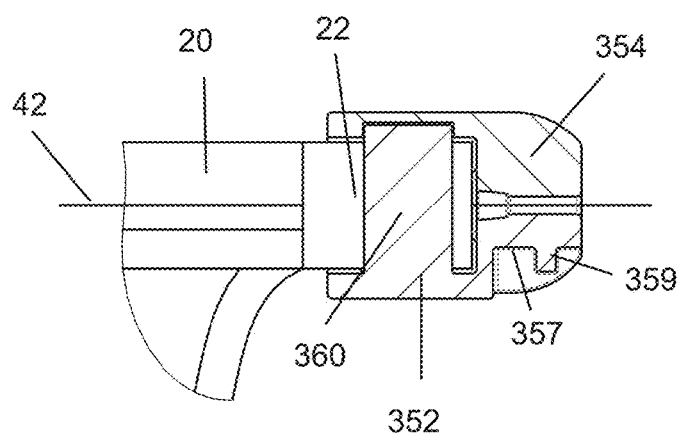
FIG. 45 is a cross sectional side view of the guide bead of FIG. 43 joined to a tissue retrieval bag.

With reference to FIGS. 43-45, in certain embodiments, the bead 350 on the retrieval bag is comprised of two halves 352, 354 that are pressed together via interference pins 356 and holes 358 or that are ultrasonically welded together. In the illustrated embodiment, the lower bead half 352 further comprises a vertical post 360 that is sized and configured to fit through a proximal end of the retrieval bag 20. The proximal end of the retrieval bag 20 includes a belt 22 that is heat sealed together and engages the post 360 on the lower bead half 352 to securely couple the bead 350 to the retrieval bag 20. The cord loop 42 can be routed on the outside of the belt. The upper bead half 354 is placed over the post to mechanically trap the belt 22 of the retrieval bag 20 within the bead halves 352, 354. Each upper and lower bead half 352, 254 can include a semi-circular groove 362 at its center along its longitudinal axis that is positioned at the proximal end of the bead 350 and is sized and configured to frictionally engage the cord loop. When the bead halves are assembled together, the semi-circular grooves 362 form a circular aperture creating a frictional fit with the cord, allowing the retrieval bag to be cinched closed and reopened. The bead halves can include angled guides 364 and mating slots for the guides surrounding the semi-circular grooves that aid with centering the cord loop within the grooves during assembly of the bead. In the illustrated embodiment, the lower bead half 352 includes the recess 357 and ledge 359 for coupling with the retaining latch.

Figure 46:
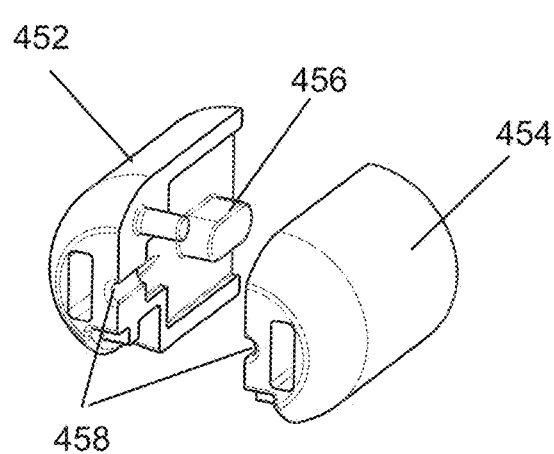
FIG. 46 is an exploded perspective view of an embodiment of guide bead for a tissue retrieval system.
Figure 47:
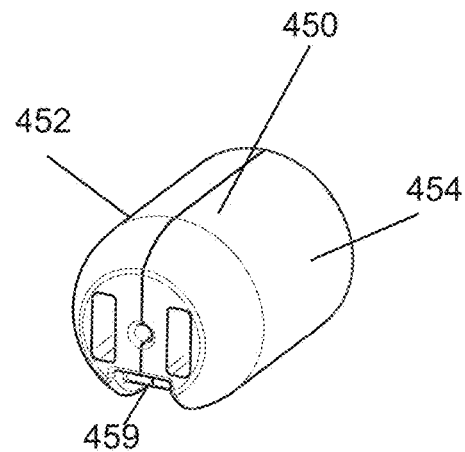
FIG. 47 is a perspective view of the guide bead of FIG. 46.
Figure 48:
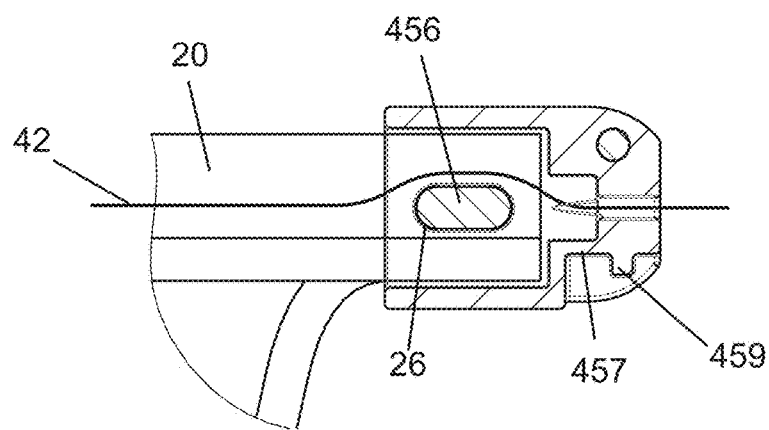
FIG. 48 is a cross sectional side view of the guide bead of FIG. 46 joined to a tissue retrieval bag.

With reference to FIGS. 46-48, in certain embodiments, the bead 450 on the retrieval bag is comprised of two halves 452, 454 that are ultrasonically welded together to securely couple the bead 450 to the retrieval bag 20. In the illustrated embodiment, the right bead half 452 includes an oval post 456 that is sized and configured to mate with a corresponding oval hole 26 in the proximal end of the retrieval bag 20. In certain embodiments, the proximal end of the retrieval bag 20 includes a die cut oval hole 26 that fits over the post in the right bead half. The cord loop 42 can be routed above or below the post. The left bead half 454 is placed over the post 456 to mechanically trap the proximal end of the retrieval bag 20 and the bead halves 452, 454 are coupled such as by ultrasonically welding. Each of the right and left bead halves 452, 454 also include a semi-circular groove 458. The semi-circular grooves 458 can be positioned at the proximal end of the bead 450. With the bead halves 452, 454 coupled (FIG. 47), the semi-circular grooves 458 collectively form a central passage through the bead 450 that can be sized to frictionally engage the cord loop. The right and left bead halves 452, 454 each include a portion of a recess 457 and ledge 459 for coupling with the retaining latch.

With continued reference to FIGS. 46-48, while the illustrated bead includes a single post positioned to retain the bag, in other embodiments, the right bead half includes two or more posts such as, for example, circular posts designed to mate with corresponding die cut holes in the proximal end of the retrieval bag. Moreover, in certain embodiments, the proximal end of the retrieval bag 20 with the die cut oval hole includes a reinforcement material to increase the retention strength of the retrieval bag to the bead. In various embodiments, the reinforcement material can be ripstop nylon, polyurethane, nylon, or other suitable materials.

Figure 49:
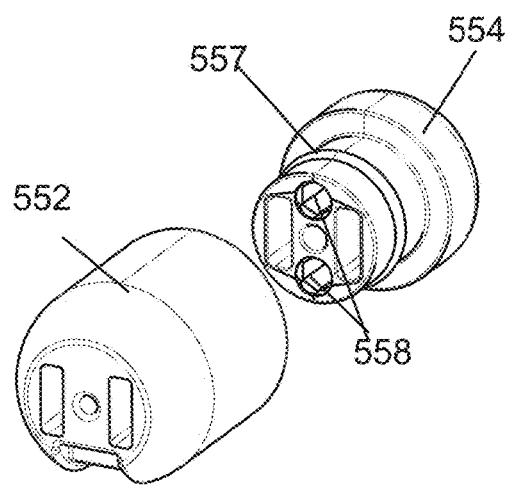
FIG. 49 is an exploded perspective view of an embodiment of guide bead for a tissue retrieval system.
Figure 50:
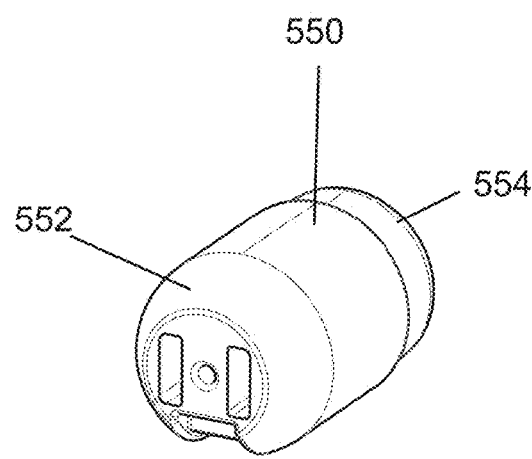
FIG. 50 is a perspective view of the guide bead of FIG. 49.
Figure 51:
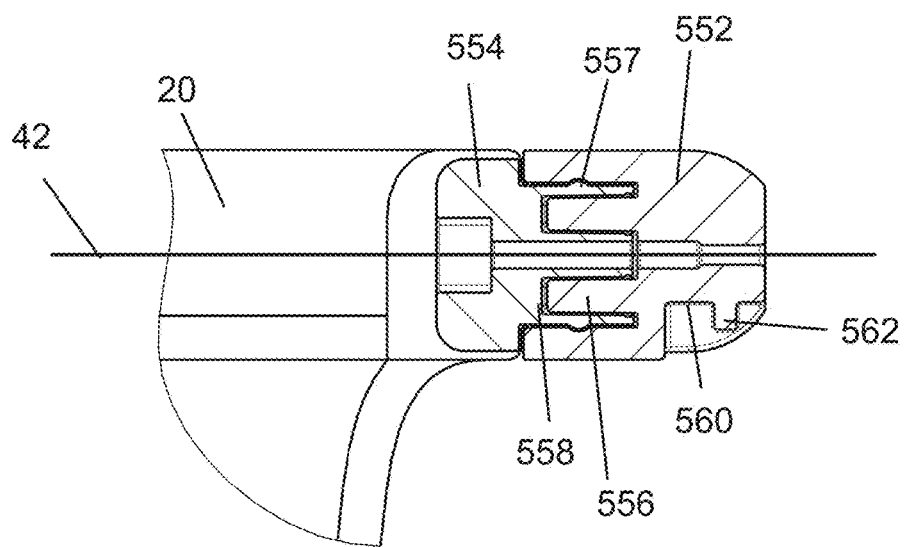
FIG. 51 is a cross sectional side view of the guide bead of FIG. 49 joined to a tissue retrieval bag.
Figure 52:
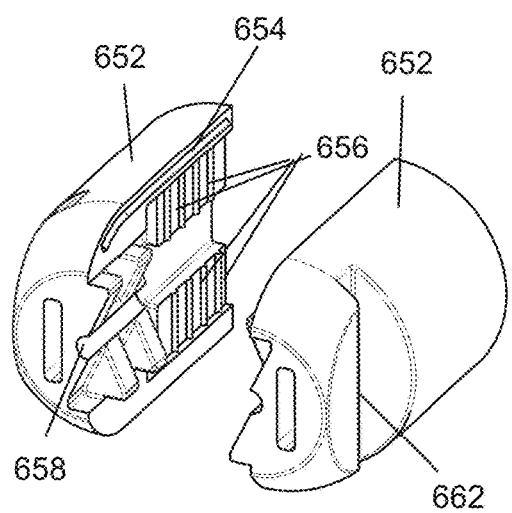
FIG. 52 is an exploded perspective view of an embodiment of guide bead for a tissue retrieval system.
Figure 53:
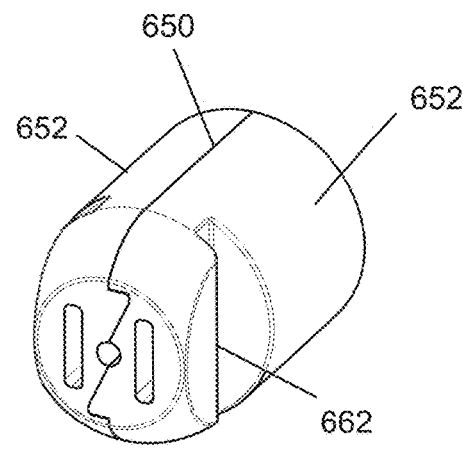
FIG. 53 is a perspective view of the guide bead of FIG. 52.
Figure 54:
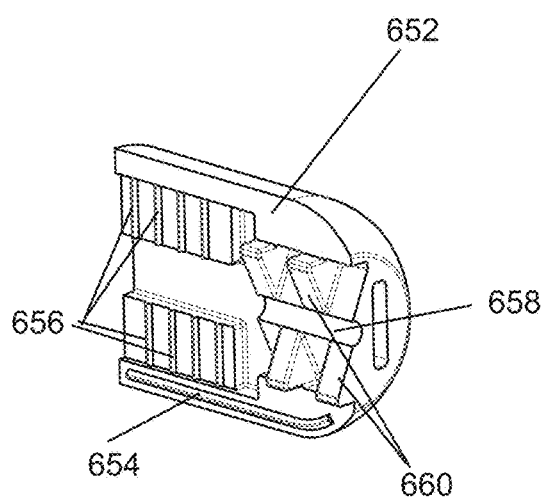
FIG. 54 is a perspective view of a guide bead portion of the guide bead of FIG. 52.
Figure 55:
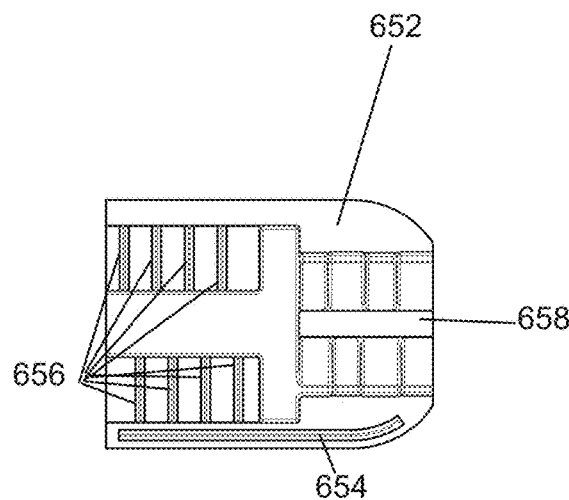
FIG. 55 is a side view of the guide bead portion of FIG. 54.

With reference to FIGS. 49-51, in certain embodiments the bead 550 on the retrieval bag is comprised of a proximal section 552 and a distal section 554 that are pressed together via interference pins 556 and holes 558. In the illustrated embodiment, the bead also includes an annular interference fit for retaining the retrieval bag 20 to the bead 550 and for affixing the proximal and distal sections 552, 554 of the bead 550 together. The distal section 554 of the bead also includes an annular ledge 557 designed to further retain the retrieval bag to the bead. To assemble the bead 550, the cord loop 42 is first threaded through each of the bead sections 552, 554 and the distal section 554 of the bead is then inserted through the distal end of a tubular portion of the retrieval bag. The proximal section 552 of the bead is then placed over the distal section 554 of the bead and the retrieval bag 20 and the two sections of the bead are pressed together trapping the tubular portion of the retrieval bag. In certain embodiments, the distal section 554 of the bead can include a slot rather than a through hole to obviate the need for threading the cord loop through the distal section 554 of the bead. In certain embodiments, an adhesive could be applied to the annular interference fit and the interference pins to further increase the retention of the retrieval bag 20 to the bead 550. In the illustrated embodiment, the proximal section 552 of the bead includes the recess 560 and ledge 562 for coupling with the retaining latch.

With reference to FIGS. 52-55, in certain embodiments, the bead 650 on the retrieval bag is comprised of two substantially identical halves 652 that are ultrasonically welded together. The bead half 652 includes an energy director 654 for ultrasonically welding the bead halves together. The bead half also includes multiple energy directors 656 for ultrasonically welding the external proximal portions of the retrieval bag between the bead halves 652. To assemble the retrieval bag to the bead 650, the retrieval bag is sandwiched between the bead halves 652, and the bead halves are subsequently ultrasonically welded to the outside of each side of the retrieval bag. The bead halves 650 can concurrently be ultrasonically welded together or can be welded together as a secondary step. The cord loop is positioned within a central recess during welding to ensure that the cord loop is not welded to the bead or the retrieval bag during assembly. The bead half also includes a semi-circular groove 658 at its center along its longitudinal axis at the proximal end of the bead that is designed to frictionally engage the cord loop. The bead half 652 includes guides 660 and mating slots for the opposing guides surrounding the semi-circular grooves 658 that aid with centering the cord loop within the grooves during assembly of the bead. The bead half includes a recess and ledge 662 for coupling with a retaining latch.

With reference to FIGS. 56-61, in certain embodiments, the handle assembly comprises a pawl assembly. The pawl assembly can be configured to provide both a secondary proximal stop mechanism and a redeployment lockout mechanism.

Figure 56:
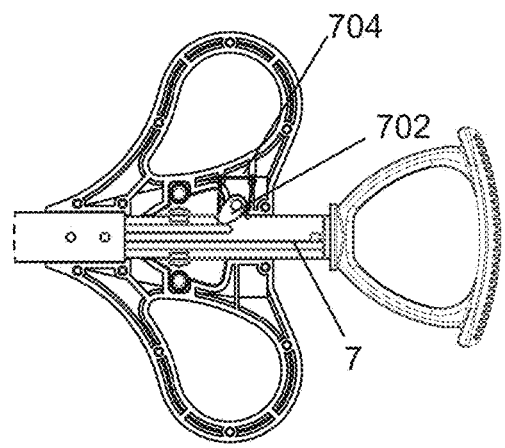
FIG. 56 is a partial cut away bottom view of a handle assembly for a tissue retrieval system with the actuator in a first deployed position.
Figure 57:
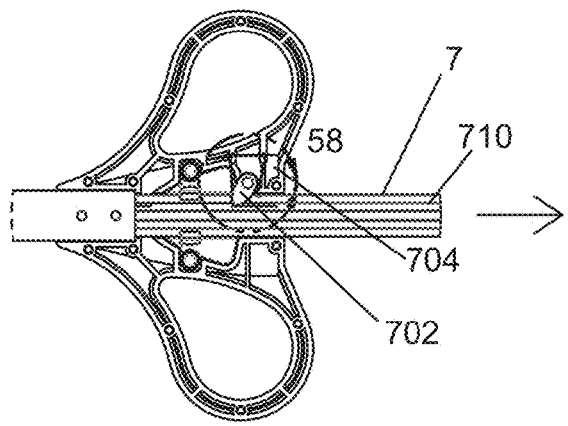
FIG. 57 is a partial cut away bottom view of the handle assembly of FIG. 56 with the actuator withdrawn to a proximal position to position the tissue retrieval bag in a stowed configuration.
Figure 58:
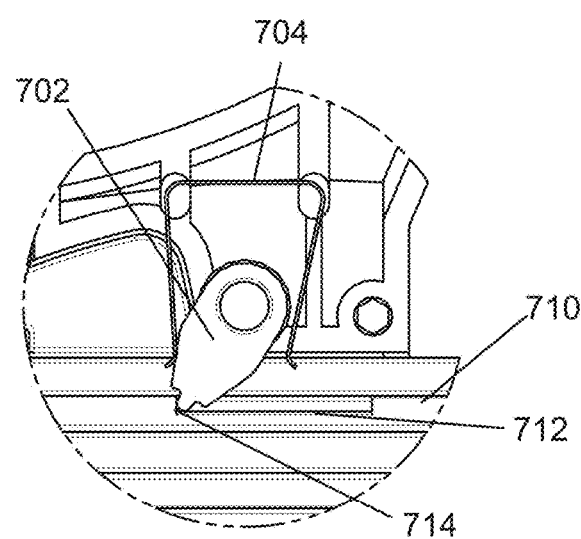
FIG. 58 is a detail view of a latching pawl of the handle assembly of FIG. 56 with the actuator withdrawn to the proximal position to position the tissue retrieval bag in a stowed configuration.

With reference to FIGS. 56-58, the pawl assembly can comprise a pawl 702 pivotally coupled to the handle assembly and a pawl spring 704. The pawl spring 704 is positioned around the pawl 702 and biases the pawl 702 to a centered position. With the actuator in its initial position slidable between the proximal position and the first deployed position for redeployable use of the retrieval bag, the pawl 702 is canted towards the distal end of the device. The actuator 7 comprises a longitudinally extending rib 710 having a first recess 712 formed therein. The pawl 702 slides along the rib 710 as the actuator is being proximally withdrawn from the first deployed position (FIG. 56). As the actuator 7 is withdrawn to retract the retrieval bag into the introducer tube, the pawl 702 will drop into the first recess 712 on the actuator 7 and will engage a distal wall 714 of the recess 712 to prevent any further proximal movement of the actuator (FIGS. 57-58). Desirably the first recess 712 is positioned on the rib at a location to engage the pawl at an actuator position corresponding to the proximal position of the actuator to ensure that the cord loop is not exposed. Thus, in certain embodiments, the handle assembly includes a secondary proximal stop mechanism preventing the retrieval bag from being withdrawn too far into the introducer tube such that the cord loop would be exposed. In other embodiments, the pawl assembly can provide a primary proximal stop mechanism and no actuator post as described with reference to FIGS. 16-22 is present in the handle assembly.

Figure 59:
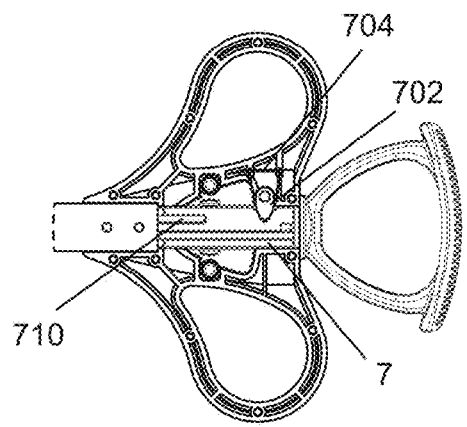
FIG. 59 is a partial cut away bottom view of the handle assembly of FIG. 56 with the actuator in a fully deployed position.
Figure 60:
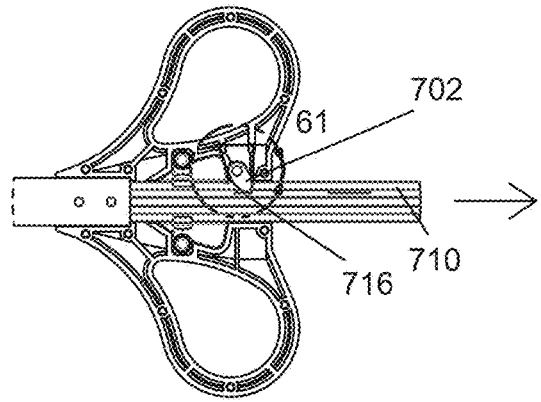
FIG. 60 a partial cut away bottom view of the handle assembly of FIG. 56 with the actuator withdrawn to position the tissue retrieval bag in a fully deployed cinched position.
Figure 61:
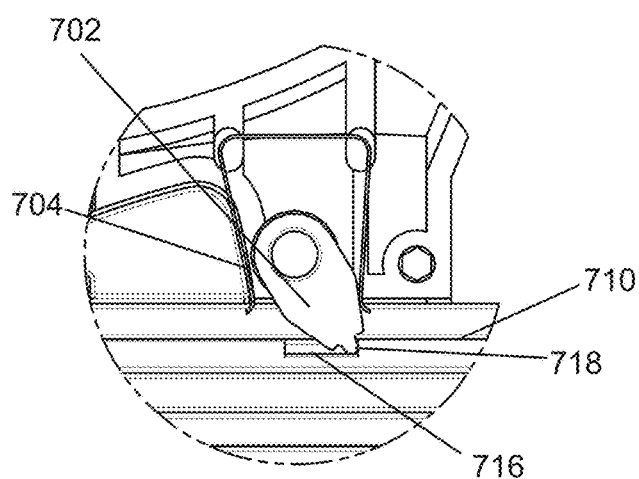
FIG. 61 is a detail view of a latching pawl of the handle assembly of FIG. 56 with the actuator withdrawn to position the tissue retrieval bag in a fully deployed cinched position.

With reference to FIGS. 59-61, when the actuator is advanced to its fully deployed position for subsequent cinching of the retrieval bag, the pawl 702 is moved off of a proximal end of the rib 710 and moves to a centered position (FIG. 59). When the actuator 7 is withdrawn proximally to begin cinching of the retrieval bag, the pawl 702 will be pivoted towards the proximal end of the device as it engages the proximal end of the rib 710. The rib 710 further comprises a second recess 716 located distal the first recess 712. When the actuator 7 is fully withdrawn with the retrieval bag cinched closed, the cord loop is exposed and the pawl 702 drops into the second recess 716 on the rib 710 (FIG. 60). The pawl 702 engages with the proximal wall 718 of the second recess 716 to prevent the actuator 7 from being advanced distally (FIG. 61). This engagement of the pawl 702 with the second recess 716 defines a redeployment lockout mechanism to prevent the actuator from being inadvertently advanced by the surgeon once the retrieval bag has been decoupled from the actuator and cinched. If the actuator were inadvertently redeployed, it could undesirably result in the support arms being advanced out of the distal end of the introducer. The pawl assembly also retains the actuator in its fully withdrawn position enabling easier removal of the cord loop from the actuator.

Thus, the illustrated embodiment of pawl assembly engages a first recess and a second recess on the rib of the actuator to provide both a proximal stop mechanism and a redeployment lockout mechanism. However, it is contemplated that in other embodiments, the rib comprises a single recess positioned such that the pawl assembly can be configured to provide only one of a proximal stop mechanism or a redeployment lockout mechanism.

Figure 62:
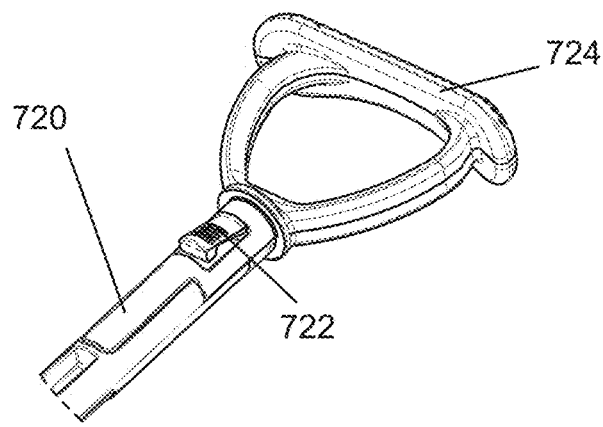
FIG. 62 is a perspective view of an embodiment of actuator handle for use in a tissue retrieval system.
Figure 63:
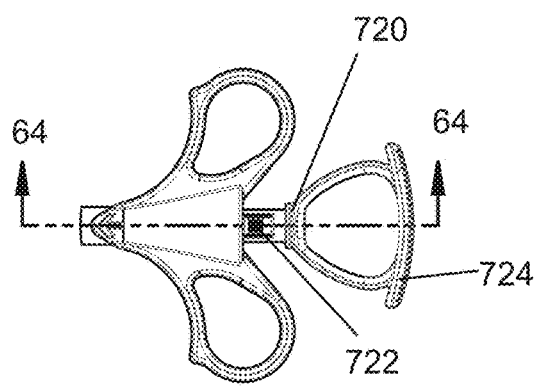
FIG. 63 is a top view of a handle assembly for a tissue retrieval system including the actuator handle of FIG. 62 with the actuator handle positioned corresponding to a tissue retrieval bag in a first deployed configuration.
Figure 64:
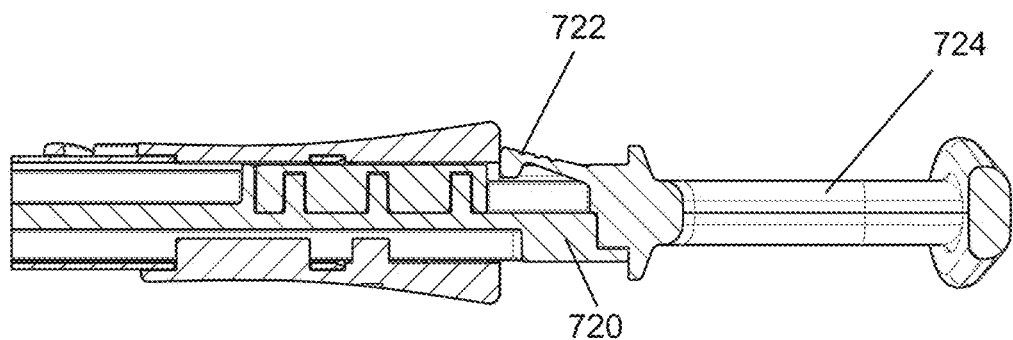
FIG. 64 is a cross-sectional side view of the handle assembly of FIG. 63.

With reference to FIGS. 62-64, in certain embodiments, a distal stop mechanism can be included in the actuator 720 rather than the handle assembly. Thus, the handle assembly can be provided without the deployment release button 110 described and illustrated with respect to FIGS. 23-28. As illustrated, the actuator 720 comprises a cantilever 722 positioned to limit the distal advancement of the actuator to the first deployed position for redeployable use of the retrieval bag. In the illustrated embodiment, the cantilever 722 is integral to a thumb loop 724 of the actuator 720, which can be pressed onto the actuator via interference pins and holes. A distal tip of the cantilever 722 contacts the upper handle during deployment of the retrieval bag to limit the travel of the actuator at the first deployed position (FIGS. 63, 64). To further advance the actuator, the cantilever 722 can be pressed downward to where it fits into an opening on the upper handle. The actuator 720 can then be advanced to its fully deployed position. In various embodiments, the thumb loop 720 including cantilever 722 can be injection molded from various polymer materials including polycarbonate, nylon, ABS, and polypropylene.

Figure 65:
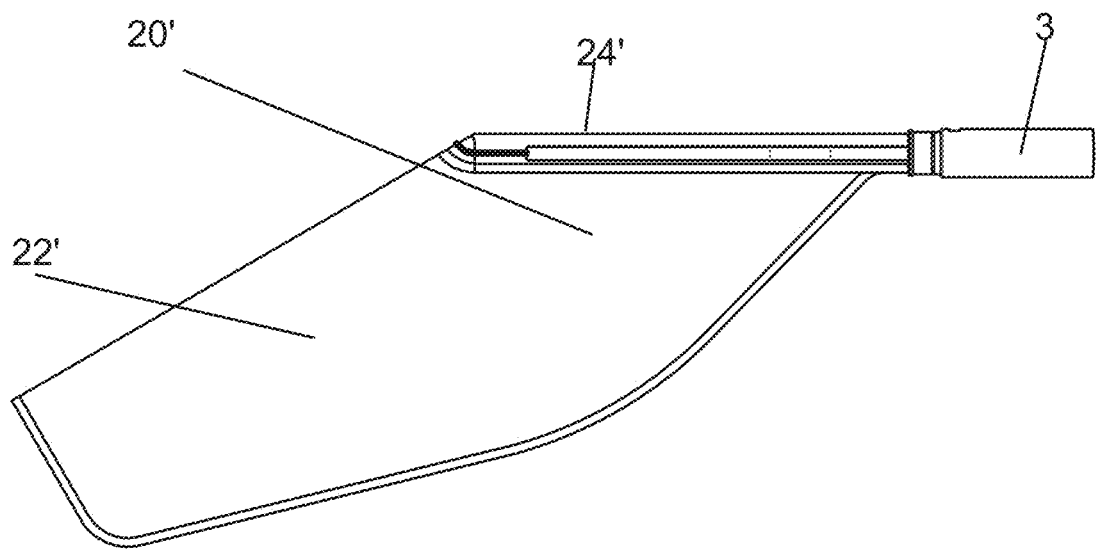
FIG. 65 is a side view of an embodiment of tissue retrieval bag at a distal end of an embodiment of tissue retrieval system with the tissue retrieval bag deployed to a first deployed position.
Figure 66:
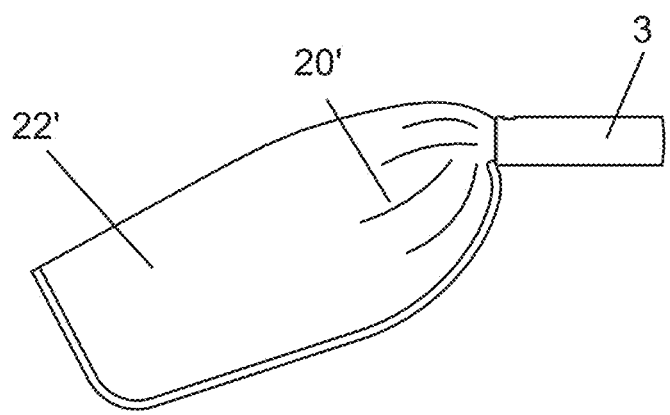
FIG. 66 is a side view of the tissue retrieval bag in a redeployable cinched configuration.

With reference to FIGS. 65-66, in certain embodiments a tissue retrieval system can comprise a tissue retrieval bag having a distally extending portion. While the tissue retrieval bags described and illustrated with respect to FIGS. 1-6 have an open end with a cuff supported by support arms and extend generally perpendicularly to a longitudinal axis of the support arms to a closed end opposite the open end, in certain embodiments, the tissue retrieval systems described herein can include a retrieval bag 20' formed with a distally extending portion 22' where the retrieval bag extends distally relative to the opening 24' of the retrieval bag. Desirably, a retrieval bag 20' with a distally-extending portion provides a more streamlined shape that reduces the force required to retract the retrieval bag 20' into the introducer 3 tube (FIG. 66) and reduces the force to extract the detached retrieval bag through the body wall of the patient relative to a tissue retrieval bag 20 without a distally-extending portion. The retrieval bag 20' with the distally extending portion 22' can also provide for a larger volume of the retrieval bag being available for small tissue specimens when the retrieval bag 20' is partially retracted into the introducer tube and the opening is reversibly closed.

Although this application discloses certain aspects of various features of redeployable tissue retrieval systems, it is contemplated that certain elements described herein can be combined in certain embodiments of tissue retrieval systems. For example, in one embodiment, a tissue retrieval system can include a handle assembly having a deployment button 111 and actuator 7 with groove 131 as described with reference to FIGS. 23B, 24B, 25B, 26B, 27B, 28B, 27C, 28C, together with a bead stop 261 with a spring-biased clip as described with reference to FIGS. 31B and 32B. However, in other embodiments, other beads, bead stops, latch members, and stop mechanisms described herein can be combined in tissue retrieval systems within the scope of the present application.

Although this application discloses certain preferred embodiments and examples, it will be understood by those skilled in the art that the present inventions extend beyond the specifically disclosed embodiments to other alternative embodiments and/or uses of the inventions and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A tissue retrieval system comprising:
a tubular introducer having a proximal end and a distal end and a lumen extending between the proximal end and the distal end;
an actuator longitudinally slidable within the lumen of the introducer, the actuator having a proximal end and a distal end;
a retaining latch at the distal end of the actuator;
a pair of support arms extending from the distal end of the actuator;
a bead distal the retaining latch, the bead releasably coupled to the retaining latch;
a tissue retrieval bag coupled to the bead and removably coupled to the support arms;
wherein the actuator is longitudinally slidable from a proximal position with the tissue retrieval bag substantially withdrawn into the introducer to a first deployed position with the tissue retrieval bag deployed from the distal end of the introducer and suspended from the support arms, and wherein the retaining latch is within the introducer and coupled to the bead in the first deployed position; and
wherein the actuator is longitudinally slidable from the first deployed position to a second deployed position distal the first deployed position such that the bead and a portion of the retaining latch is distal the distal end of the introducer and the bead is releasable from the retaining latch.

2. The tissue retrieval system of claim 1, wherein the actuator is repeatably slidable between the proximal position and the first deployed position with the retaining latch coupled to the bead.

3. The tissue retrieval system of claim 1, further comprising a bead stop distal the actuator and proximal the bead.

4. The tissue retrieval system of claim 3, wherein the bead stop engages the introducer with the actuator in the second deployed position to prevent the bead from reentering the introducer.

5. The tissue retrieval system of claim 4, wherein the introducer comprises an aperture adjacent the distal end and the bead stop comprises a cantilever spring arm positioned to engage the aperture with the actuator in the second deployed position.

6. The tissue retrieval system of claim 3, wherein the retaining latch comprises an arm extending distally to a distal end and the bead comprises a ledge formed therein and wherein the distal end of the arm of the retaining latch is releasably engageable with the ledge on the bead.

7. The tissue retrieval system of claim 6, wherein the bead stop comprises a channel formed therein and wherein the arm of the retaining latch extends through the channel of the bead stop.

8. A tissue retrieval system comprising:
a tubular introducer having a proximal end and a distal end and a lumen extending between the proximal end and the distal end;
a handle assembly at the proximal end of the introducer;
an actuator longitudinally slidable within the lumen of the introducer, the actuator having a proximal end and a distal end;
a tissue retrieval bag releasably coupled to the distal end of the actuator, wherein the handle assembly comprises a proximal stop mechanism and a distal stop mechanism such that the actuator is repeatably longitudinally slidable between a proximal position in which the tissue retrieval bag is withdrawn into the distal end of the introducer and a first deployed position in which the tissue retrieval bag is deployed from the distal end of the introducer and coupled to the actuator;
wherein the distal stop mechanism comprises a deployment latch corresponding to the first deployed position;
wherein the deployment latch is selectively releasable such that the actuator is slidable distally from the first deployed position to a second deployed position in which the tissue retrieval bag is deployed from the distal end of the introducer and released from the actuator; and
wherein the actuator comprises at least one lateral protrusion, wherein the deployment latch comprises a deployment release button coupled to at least one latch tab, and wherein with the deployment latch in a latched configuration, the at least one latch tab is positioned to block distal movement of the at least one lateral protrusion of the actuator.

9. The tissue retrieval system of claim 8, wherein the deployment release button is movable to a released position such that the at least one latch tab is spaced apart from the at least one lateral protrusion of the actuator to allow distal movement of the actuator from the first deployed position to the second deployed position.

10. A tissue retrieval system comprising:
a tubular introducer having a proximal end and a distal end and a lumen extending between the proximal end and the distal end;
a handle assembly at the proximal end of the introducer;
an actuator longitudinally slidable within the lumen of the introducer, the actuator having a proximal end and a distal end;
a tissue retrieval bag releasably coupled to the distal end of the actuator, wherein the handle assembly comprises a proximal stop mechanism and a distal stop mechanism such that the actuator is repeatably longitudinally slidable between a proximal position in which the tissue retrieval bag is withdrawn into the distal end of the introducer and a first deployed position in which the tissue retrieval bag is deployed from the distal end of the introducer and coupled to the actuator; and
wherein the actuator comprises a ledge positioned thereon such that the ledge is within the handle assembly when the actuator is in the proximal position, and wherein the proximal stop mechanism comprises an actuator post positioned to engage the ledge of the actuator.

11. The tissue retrieval system of claim 10, wherein the distal stop mechanism is selectively releasable such that the actuator is slidable distally from the first deployed position to a second deployed position in which the tissue retrieval bag is deployed from the distal end of the introducer and released from the actuator, and wherein with the actuator in the second deployed position, the actuator post is repositioned to be spaced apart from the ledge of the actuator when the actuator is withdrawn proximally.

12. The tissue retrieval system of claim 10, wherein the actuator comprises a longitudinally extending rib having a first recess formed therein, wherein the handle assembly comprises a secondary proximal stop mechanism comprising a pawl positioned to longitudinally slide along the rib of the actuator as the actuator is slid proximally from the first deployed position to the proximal position and engage the first recess with the actuator is the proximal position.

13. The tissue retrieval system of claim 12, wherein the distal stop mechanism is selectively releasable such that the actuator is slidable distally from the first deployed position to a second deployed position in which the tissue retrieval bag is deployed from the distal end of the introducer and released from the actuator, and wherein the actuator is withdrawable from the second deployed position proximally past the proximal position.

14. The tissue retrieval system of claim 13 wherein the longitudinally extending rib of the actuator comprises a second recess formed therein, and wherein advancing the actuator distally from a position proximally past the proximal stop seats the pawl in the second recess to prevent redeployment of the actuator.

* * * * *

UNITED STATES PATENT AND TRADEMARK OFFICE
CERTIFICATE OF CORRECTION

PATENT NO. : 11,547,428 B2
APPLICATION NO. : 17/098202
DATED : January 10, 2023
INVENTOR(S) : Scott V. Taylor, Nicholas J. Fox and Quoc P. Tran It is certified that error appears in the above-identified patent and that said Letters Patent is hereby corrected as shown below:

On the Title Page

Item (54): Please change "REDEPLOY ABLE TISSUE RETRIEVAL SYSTEM" to --REDEPLOYABLE TISSUE RETRIEVAL SYSTEM--.

In the Specification

Column 1, Line 1: Please change "REDEPLOY ABLE" to --REDEPLOYABLE--.

Signed and Sealed this
Twenty-first Day of February, 2023

Katherine Kelly Vidal
*Director of the United States Patent and Trademark Office*